(12) United States Patent
Martinez-Santiago et al.

(10) Patent No.: US 8,465,552 B2
(45) Date of Patent: Jun. 18, 2013

(54) THICKENED HAIR COLORS

(75) Inventors: Jose Martinez-Santiago, New York, NY (US); Anand Ramchandra Mahadeshwar, Pompton Lakes, NJ (US)

(73) Assignee: ISP Investments, Inc., Wilmington, DE (US)

( * ) Notice: Subject to any disclaimer, the term of this patent is extended or adjusted under 35 U.S.C. 154(b) by 0 days.

(21) Appl. No.: 13/399,566

(22) Filed: Feb. 17, 2012

(65) Prior Publication Data

US 2012/0317734 A1 Dec. 20, 2012

Related U.S. Application Data

(60) Provisional application No. 61/444,388, filed on Feb. 18, 2011.

(51) Int. Cl.
*A61Q 5/10* (2006.01)

(52) U.S. Cl.
USPC ............. 8/405; 8/406; 8/408; 8/410; 8/411; 8/421; 8/435; 8/552; 8/553

(58) Field of Classification Search
USPC ............. 8/405, 406, 408, 410, 411, 421, 435, 8/552, 553
See application file for complete search history.

(56) References Cited

U.S. PATENT DOCUMENTS 3,398,094 A * 8/1968 Blatz et al. .................... 507/219

* cited by examiner

*Primary Examiner* — Eisa Elhilo
(74) *Attorney, Agent, or Firm* — William J. Davis; Thompson Hine LLP

(57) ABSTRACT

Described herein are beneficial hair color mixes comprising lightly- to moderately-crosslinked PVP. The color mix may be derived from one, two, or more parts, and the color mix exhibits satisfactory viscosity, stability, and formulation compatibility.

20 Claims, 24 Drawing Sheets

THICKENED HAIR COLORS

CROSS REFERENCE TO RELATED APPLICATION

The present application claims the benefit of U.S. provisional patent application 61/444,388 filed on Feb. 18, 2011, the contents of which are hereby incorporated by reference.

BACKGROUND

The present application relates to compositions and a method for coloring hair.

Consumers use hair color products for a variety of purposes, usually focused on enhancing their appearance. A new hair color may be desired for an evening (for example, a holiday or party) or for a longer period of time (for example, until the hair grows out). To meet these needs, three categories of hair colors have been developed: temporary, semi-permanent, and permanent. This application relates to all classifications of hair colors.

Temporary hair color products can be removed by shampooing, which offers appeal to consumers wanting the option to change hair color often. To achieve this effect a mild hair color treatment can be used, which causes minimal damage to the hair. However, temporary colors can stains and leach due to rain, high humidity, or perspiration.

Unlike their temporary counterpart, semi-permanent hair colors are removed from the hair gradually with repeated washing, and typically last for about 4 to 6 shampoos. Semi-permanent hair color products may be provided in the form of a rinse, and they cause minimal damage to the hair.

Permanent hair colors, also known as oxidative hair color, utilize a different chemical delivery system than the other two methods. Typically, these products are sold in the form of a kit that has at least two parts. The first part is a color base, or a dye base, and usually is packed in a container having an aqueous alkaline composition in the liquid, gel, or crème form that contains oxidative dyes, an alkalizing agent which is most often ammonium hydroxide, and optionally one or more fatty acids. The other part is the developer, which contains an oxidizing agent, usually hydrogen peroxide. The parts of the permanent hair color kit are mixed immediately prior to use to create the color mix, which is then applied to hair. Directions for the most popular permanent hair colors suggest the color mix be left on hair for about 20 to 60 minutes, and then rinsed off with water. Consumers expect permanent hair colors to last longer than temporary and semi-permanent hair colors, and may in fact last for six weeks or more.

Permanent hair color kits offered for sale often contain more than two components. For example, additional parts may be included to help nuance the final hair color, impart conditioning, and/or shine. Like two-part hair colors, these additional components are blended with the color base and developer before applying to hair. In some hair color products a post-treatment conditioner also is provided, which is worked into hair after coloring and then removed by rinsing in the shower.

Consumers also expect many performance attributes from hair color products. The desired color mix should be easy to prepare from the various components, not drip or run (for example, onto the face or into the eyes), have a pleasing texture, be easy to spread/distribute through the hair, and rinse out easily. To achieve these qualities, the manufacturers of hair colors require hair color ingredients that are non-toxic, broadly compatible, and extend formulation flexibility. However, hair color, especially the color mix, are difficult to thicken, and the available methods can restrict formulation flexibility.

The present inventors have observed that because the viscosity of hair color products can change (for example, on storage), it may be difficult to obtain a homogeneous mixture when these compositions are mixed. In addition, their inconsistency may make them difficult to use.

For example, a review of popular hair color products shows the most common thickeners are: (a) fatty alcohols, amides, and acids that precipitate at the alkaline pH of the color mix, (b) polymers that are alkali swellable, like crosslinked poly(acrylic acid), and (c) polymer/surfactant combinations that interact to create associative complexes.

Thickeners in the prior art and used in other personal care arts may not perform in hair colors. One deficiency is formulation instability due to the change in pH once the color base and developer are mixed. Thickeners may exhibit stringiness or incompletely dissolve and form "fish eyes." Other thickeners may not make it possible to obtain intense and chromatic shades of low selectivity and good fastness and to offer a good cosmetic condition to the treated hair. Moreover, it has been observed that most of the ready-to-use dyeing compositions of the prior art comprising at least one oxidation dye, and a thickening system may not allow a sufficiently precise application without running or drops in viscosity over time. Hence, needed is an improved thickening system that promotes an appropriate viscosity to avoid dripping and running of the color mix product, is stable, and does not interfere with color shade, coverage, or uniformity.

As it will be explained, the present application is related to lightly- to moderately-crosslinked poly(N-vinyl-2-pyrrolidone) (PVP). This polymer was first introduced in U.S. Pat. No. 5,073,614. In that patent it is taught to be the precipitation polymerization product of N-vinyl-2-pyrrolidone monomer in an organic solvent, such as an aliphatic hydrocarbon solvent (preferably cyclohexane or heptane) or an aromatic hydrocarbon (such as toluene) in the presence of about 0.2% to 1% by weight of a crosslinking agent. The fine, white powders thus produced have an aqueous gel volume of about 15 mL to 150 mL of polymer, and a Brookfield viscosity in 5% aqueous solution of at least about 10,000 cP.

Lightly- to moderately-crosslinked PVP also was the subject of U.S. Pat. No. 5,139,770. Examples are provided in this patent for a cream rise (pH of 4), a hair conditioner (pH of 4), and a blow dry styling lotion (pH of 6), which have been pH-adjusted by the addition of citric acid or phosphoric acid.

U.S. Pat. No. 5,716,634 teaches a lightly-crosslinked N-vinyl lactam polymer in form of stable, clear, flowable, homogenized hydrogel, may be used as a carrier for cosmetic/pharma active for hair or skin use. Also, the production of lightly- to moderately-crosslinked PVP in an oil-in-water or water-in-oil emulsion is taught in U.S. Pat. No. 6,177,068.

Three pending PCT applications also disclose lightly- to moderately-crosslinked PVP in the personal care arts. WO 2010/105050 teaches substantially anhydrous, substantially non-alcoholic personal care compositions having the above-named polymer. WO 2010/105052 provides for compositions having at least: (a) one personal care acid at 0.5% addition level or more, or one pharmaceutical acid at 0.5% addition level or more, and (b) lightly- to moderately-crosslinked PVP. The third application, WO 2010/105030 claims composition comprising: (a) at least one active ingredient selected from the group consisting of an antiperspirant active and a deodorant active; and (b) a thickening agent, wherein the thickening agent comprises a strongly swellable, lightly to moderately crosslinked polyvinyl pyrrolidone.

A summary of some properties of light- to moderately-crosslinked poly(N-vinyl-2-pyrrolidone) is given in Shih, J. S., "Characteristics of lightly crosslinked poly(N-vinylpyrrolidone)," Polymer Materials: Science & Engineering Preprint, 72, 374, 1995.

Still more information on this lightly crosslinked poly(N-vinyl-2-pyrrolidone) polymer is given in the following U.S. Pat. Nos. 5,162,417; 5,312,619; 5,622,168; 5,564,385; and 6,582,711.

The three U.S. Pat. Nos. ('614, '770, '634), the three published PCT patent applications ('050, '052, '030), and the Shih article mentioned in the above paragraphs are hereby incorporated in their entirety by reference.

SUMMARY

New hair color compositions have been discovered that resolve problems noted in the prior art in thickening, stabilizing, and presenting rich color palettes for hair colors. The inventors have found that lightly- to moderately-crosslinked PVP effectively thickens the color base and/or the developer, and the blended color mix. This polymer lends itself to creating thick and aesthetically-pleasing color mixes that are stable and do not interfere with color dyes. Even more surprising, it appears that lightly- to moderately-crosslinked PVP forms associative complexes with alcohols, acids, and surfactants, building greater viscosity in the hair color product than one would expect. Lastly, the lightly- to moderately-crosslinked PVP also is useful in hair color formulations having suspended inert particles, such as those added to enhancing the bleaching effect on keratin fibers.

In accordance with one embodiment, the present application describes a composition for coloring hair comprising either: A) a system comprising a color base and a developer wherein at least one of the color base and the developer comprises lightly- to moderately-crosslinked PVP; or B) a color mix wherein the color mix comprises lightly- to moderately-crosslinked PVP. The lightly- to moderately-crosslinked PVP may be present in an amount of up to 10% based on the total weight of the composition or the individual components. In particular embodiments, the lightly- to moderately-crosslinked PVP may be present in amounts ranging from about 0.5% to 8%, more particularly from about 2% to 6% and in certain embodiments from about 2.5% to 5% by weight.

DETAILED DESCRIPTION

Figure 1:
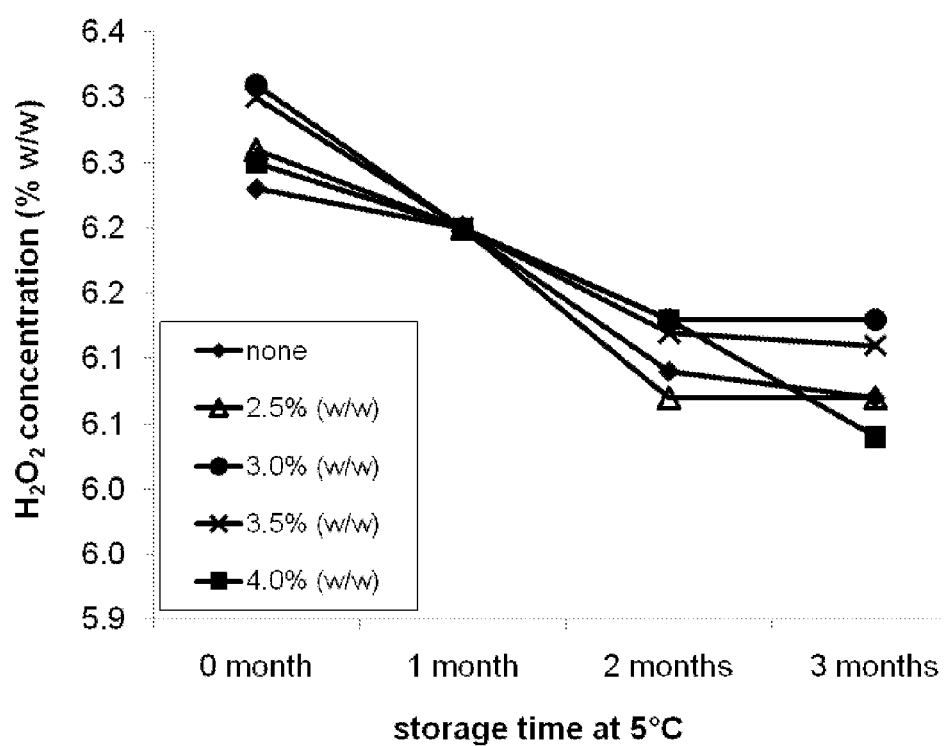
FIG. 1 is a graph of hydrogen peroxide concentration as a function of storage time at 5° C. for samples produced in accordance with Example 1.
Figure 2:
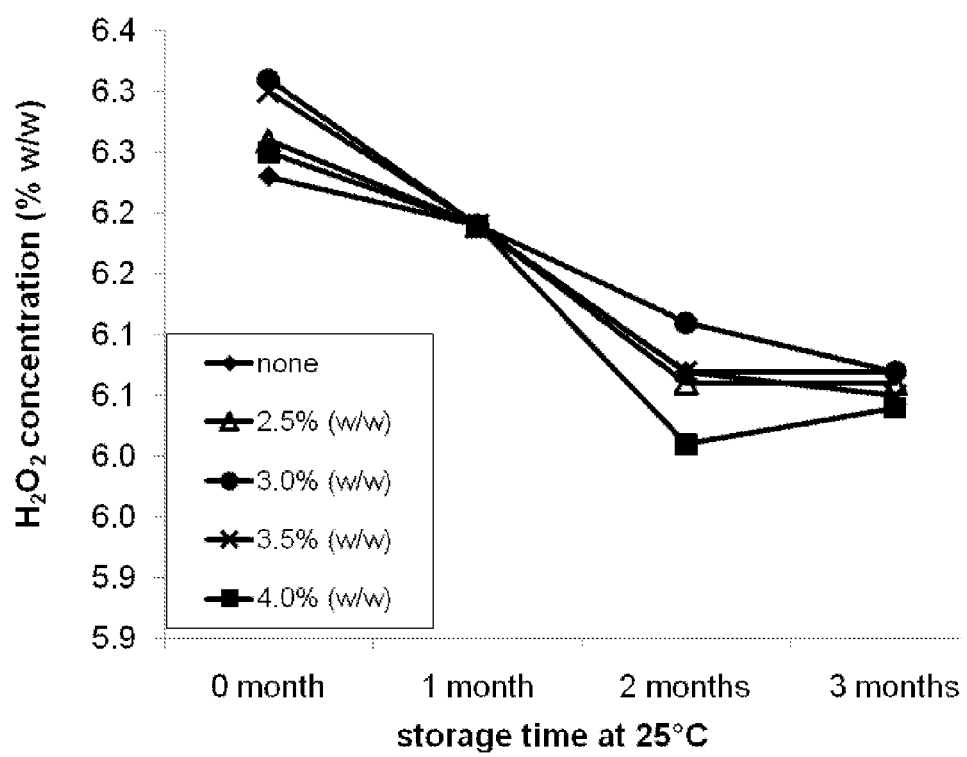
FIG. 2 is a graph of hydrogen peroxide concentration as a function of storage time at 25° C. for samples produced in accordance with Example 1.
Figure 3:
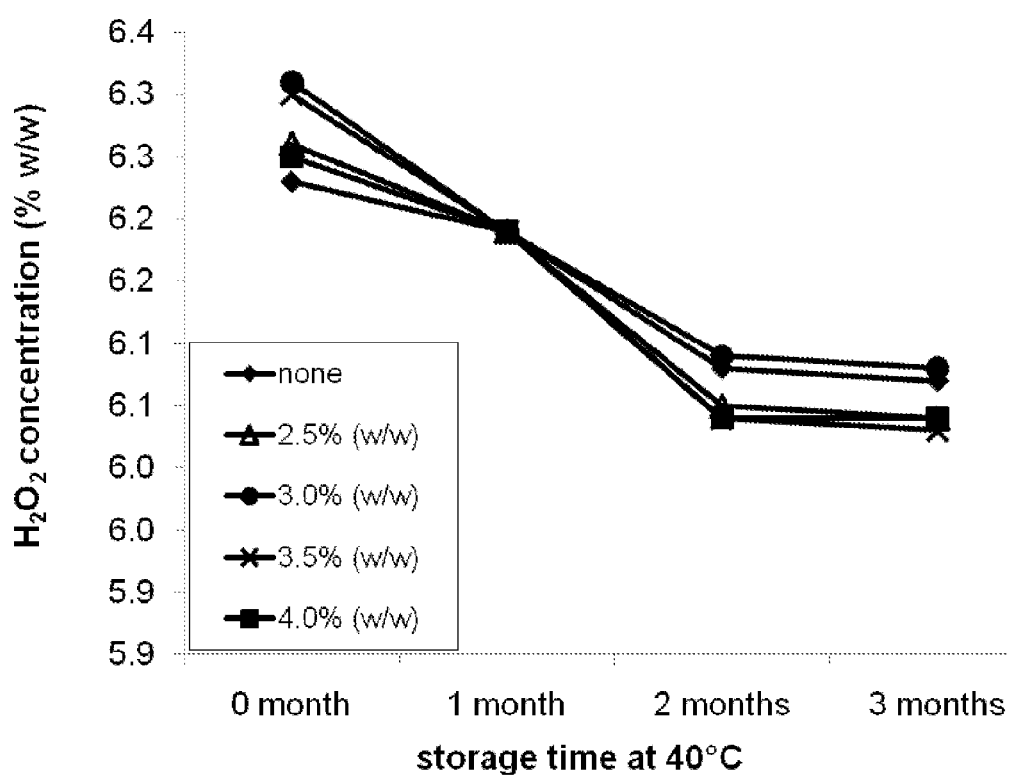
FIG. 3 is a graph of hydrogen peroxide concentration as a function of storage time at 40° C. for samples produced in accordance with Example 1.
Figure 4:
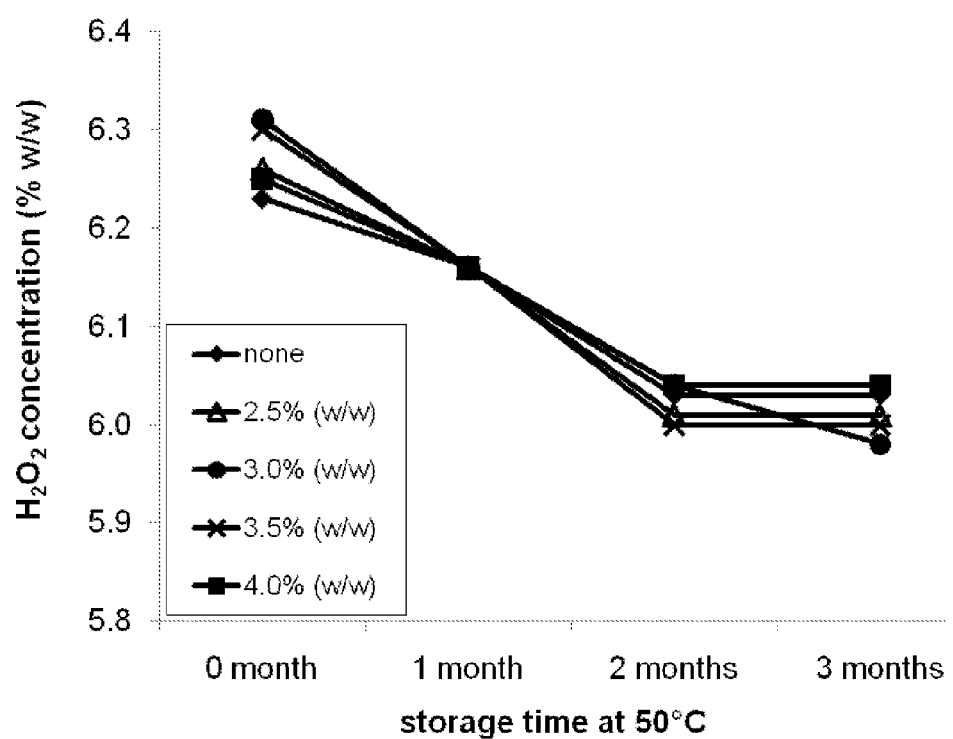
FIG. 4 is a graph of hydrogen peroxide concentration as a function of storage time at 50° C. for samples produced in accordance with Example 1.
Figure 5:
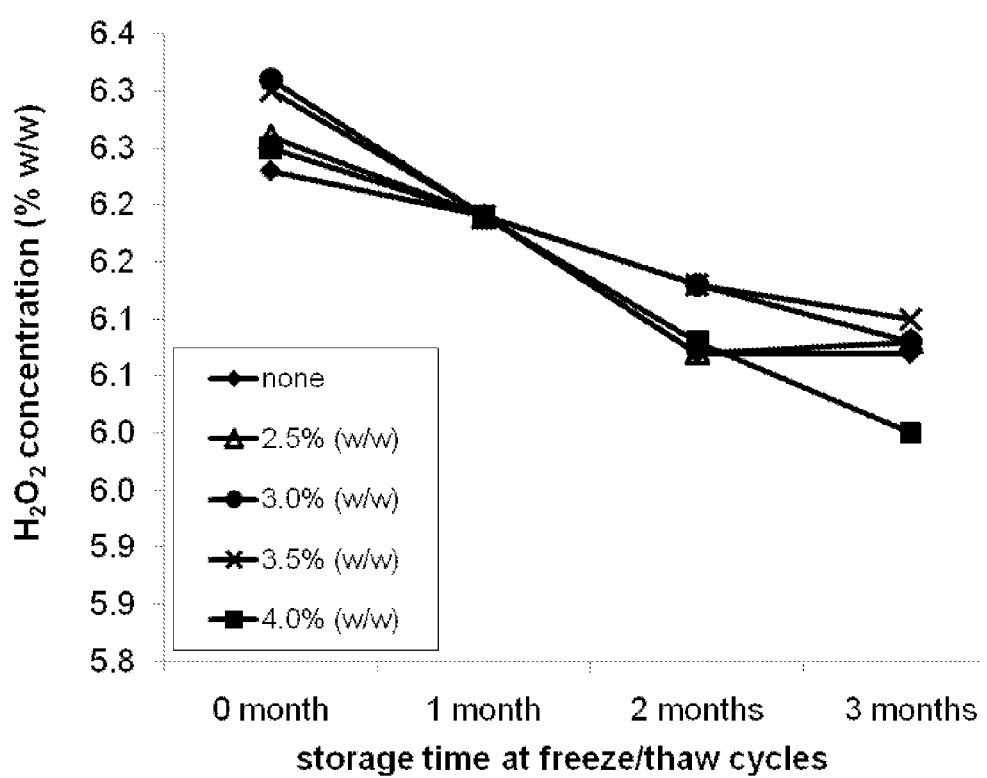
FIG. 5 is a graph of hydrogen peroxide concentration as a function of storage time at freeze/thaw cycles for samples produced in accordance with Example 1.
Figure 6:
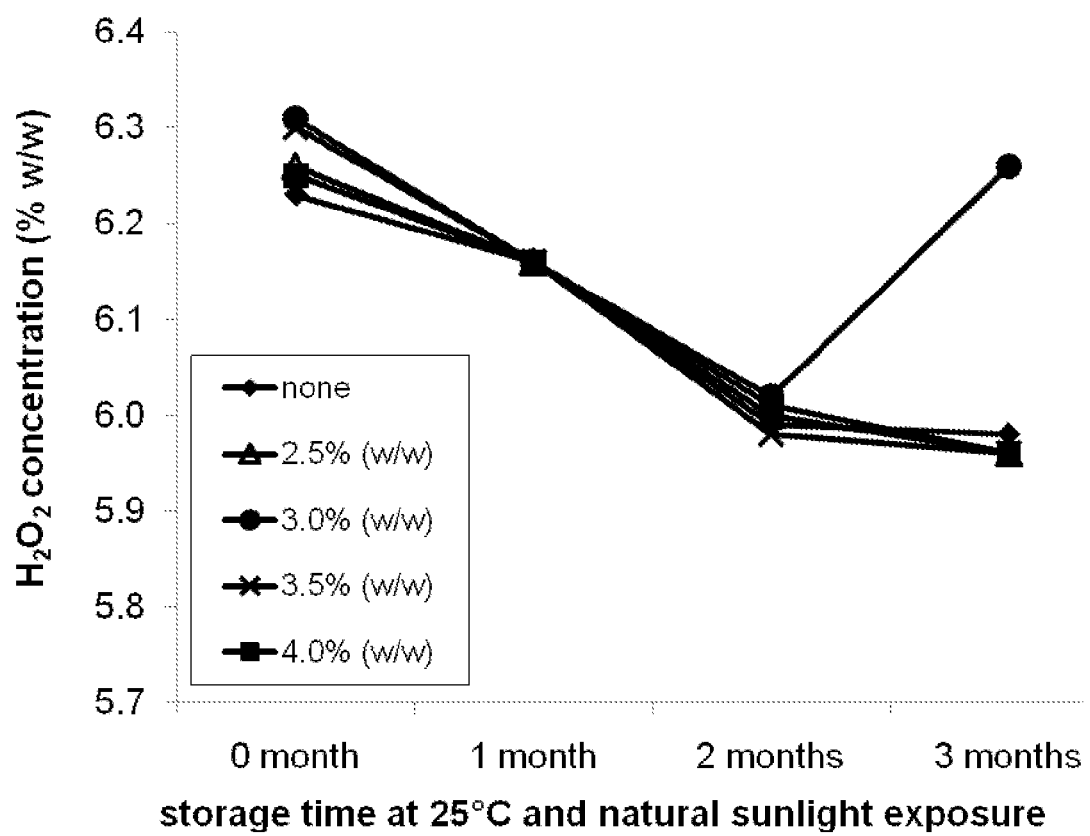
FIG. 6 is a graph of hydrogen peroxide concentration as a function of storage time at 25° C. and exposed to natural sunlight for samples produced in accordance with Example 1.
Figure 7:
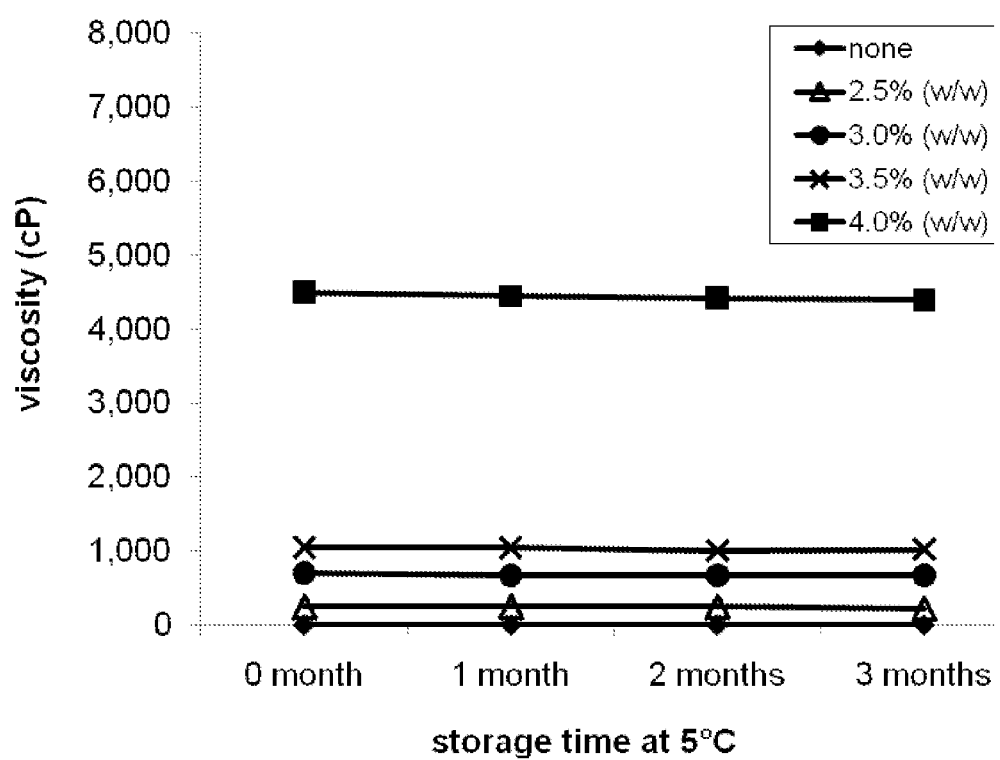
FIG. 7 is a graph of hydrogen peroxide solution viscosity as a function of storage time at 5° C. for samples produced in accordance with Example 2.
Figure 8:
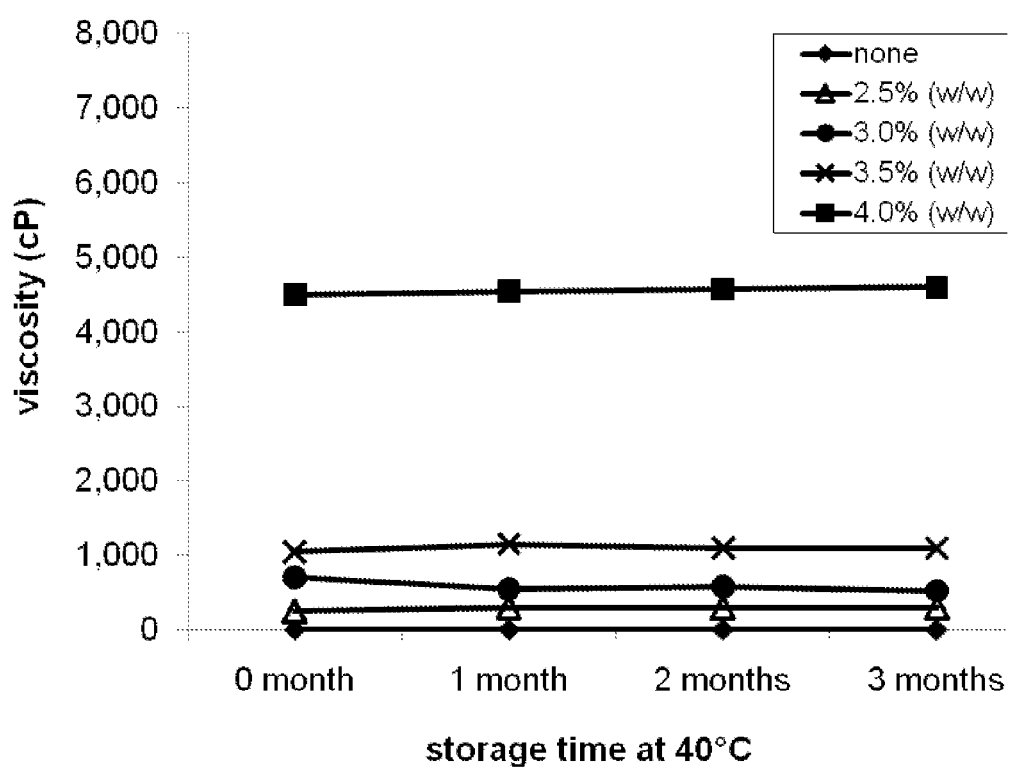
FIG. 8 is a graph of hydrogen peroxide solution viscosity as a function of storage time at 40° C. for samples produced in accordance with Example 2.
Figure 9:
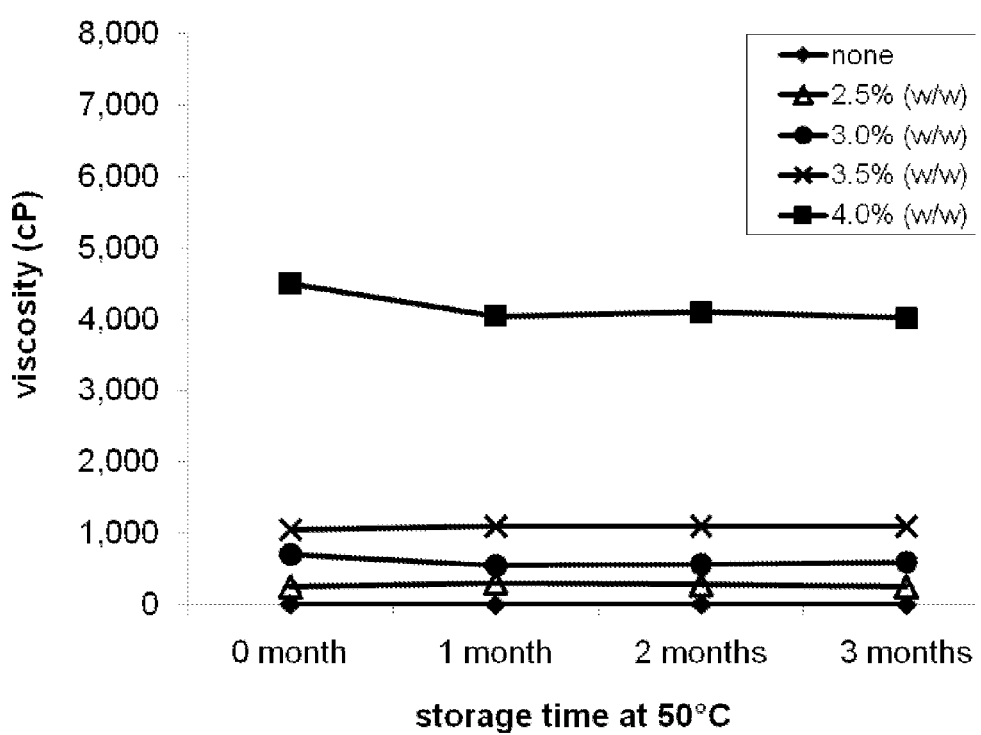
FIG. 9 is a graph of hydrogen peroxide solution viscosity as a function of storage time at 50° C. for samples produced in accordance with Example 2.
Figure 10:
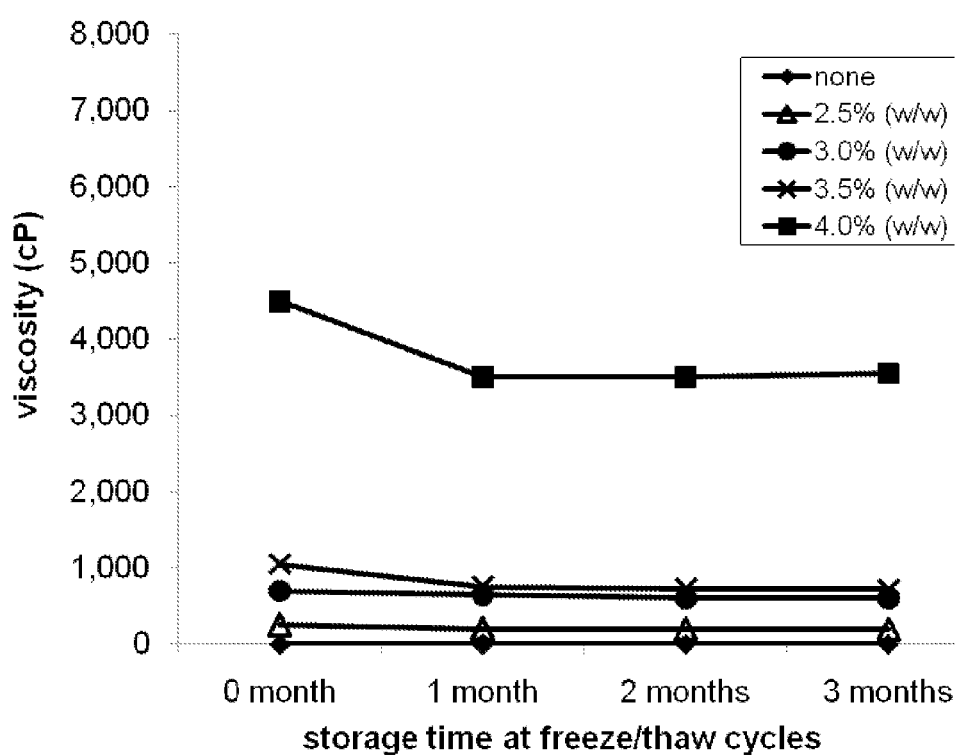
FIG. 10 is a graph of hydrogen peroxide solution viscosity as a function of storage time at freeze/thaw cycles for samples produced in accordance with Example 2.
Figure 11:
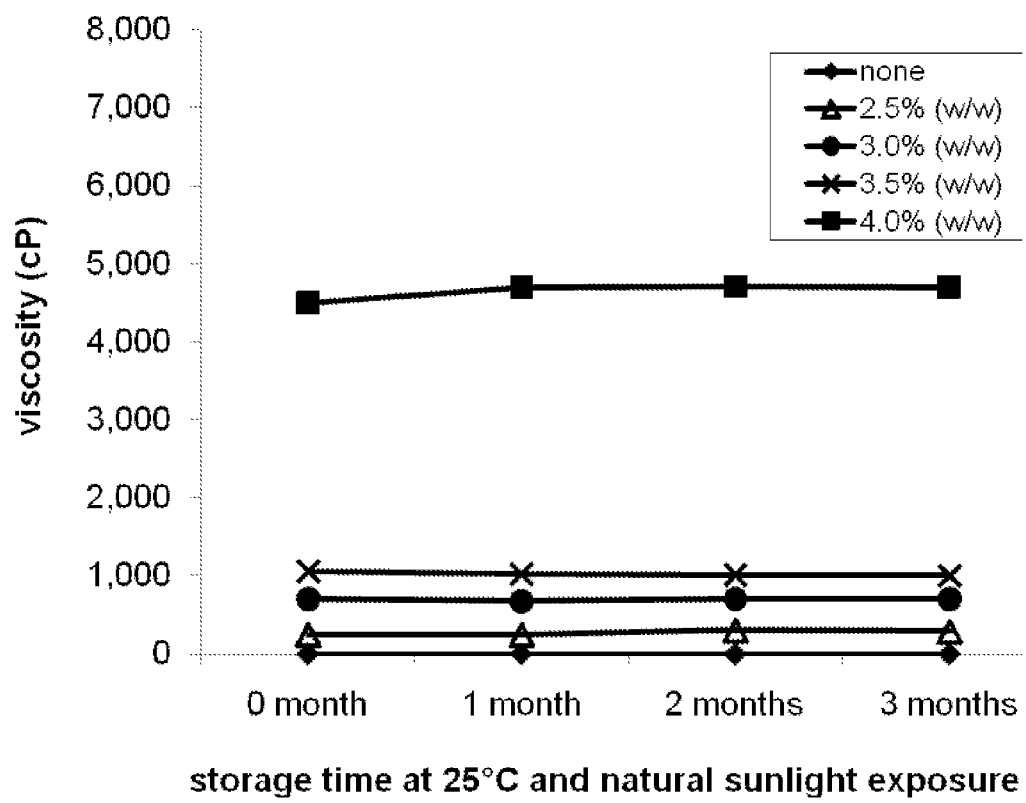
FIG. 11 is a graph of hydrogen peroxide solution viscosity as a function of storage time at 25° C. and exposed to natural sunlight for samples produced in accordance with Example 2.
Figure 12:
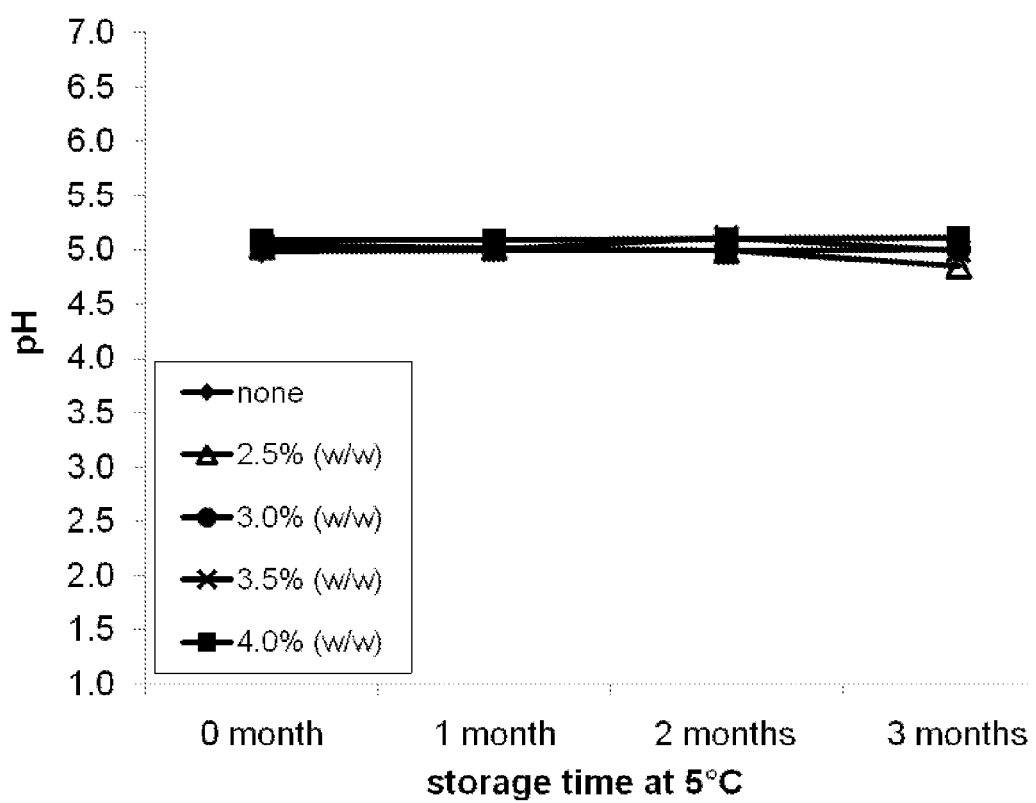
FIG. 12 is a graph of hydrogen peroxide pH as a function of storage time at 5° C. for samples produced in accordance with Example 2.
Figure 13:
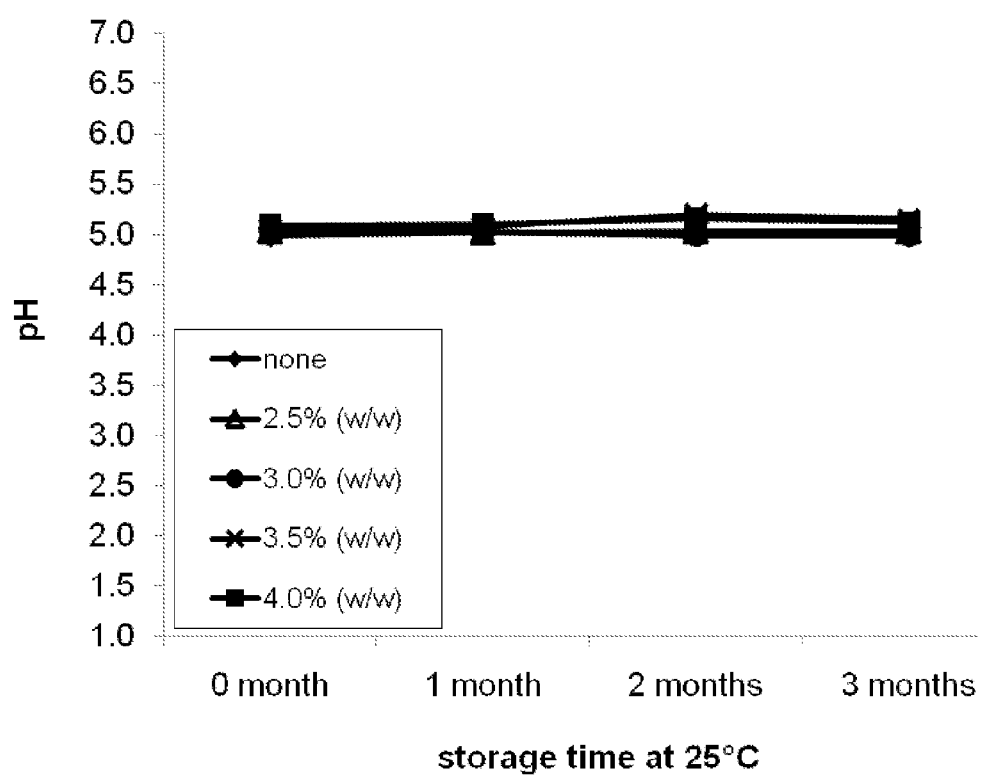
FIG. 13 is a graph of hydrogen peroxide pH as a function of storage time at 25° C. for samples produced in accordance with Example 3.
Figure 14:
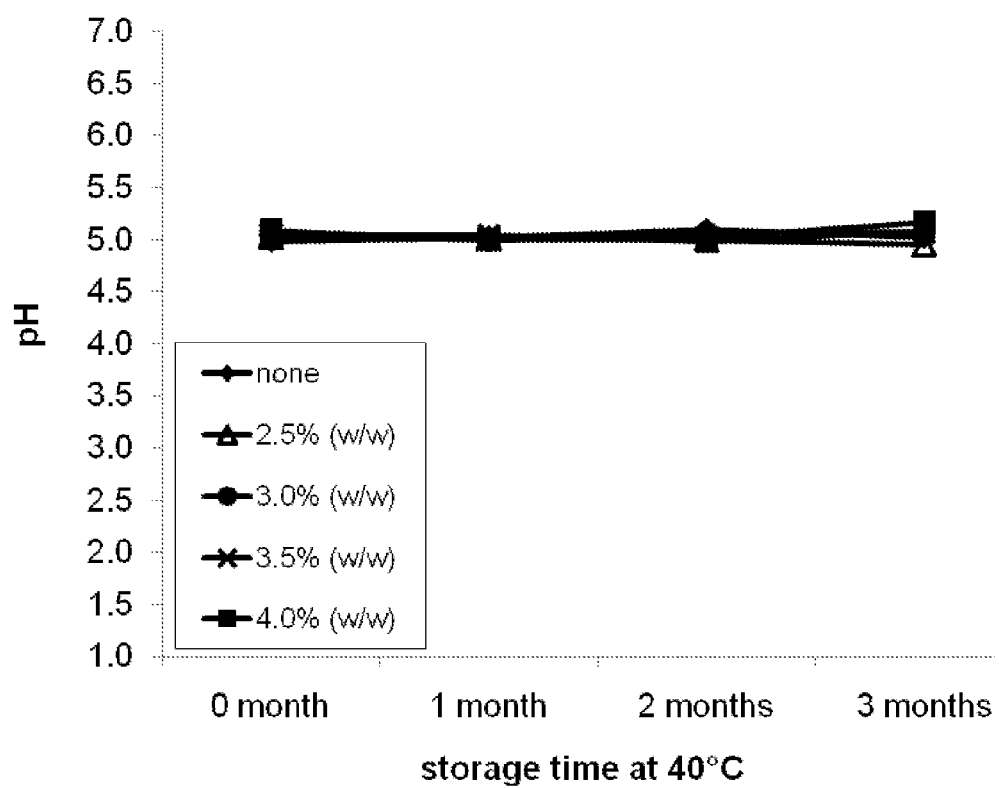
FIG. 14 is a graph of hydrogen peroxide pH as a function of storage time at 40° C. for samples produced in accordance with Example 3.
Figure 15:
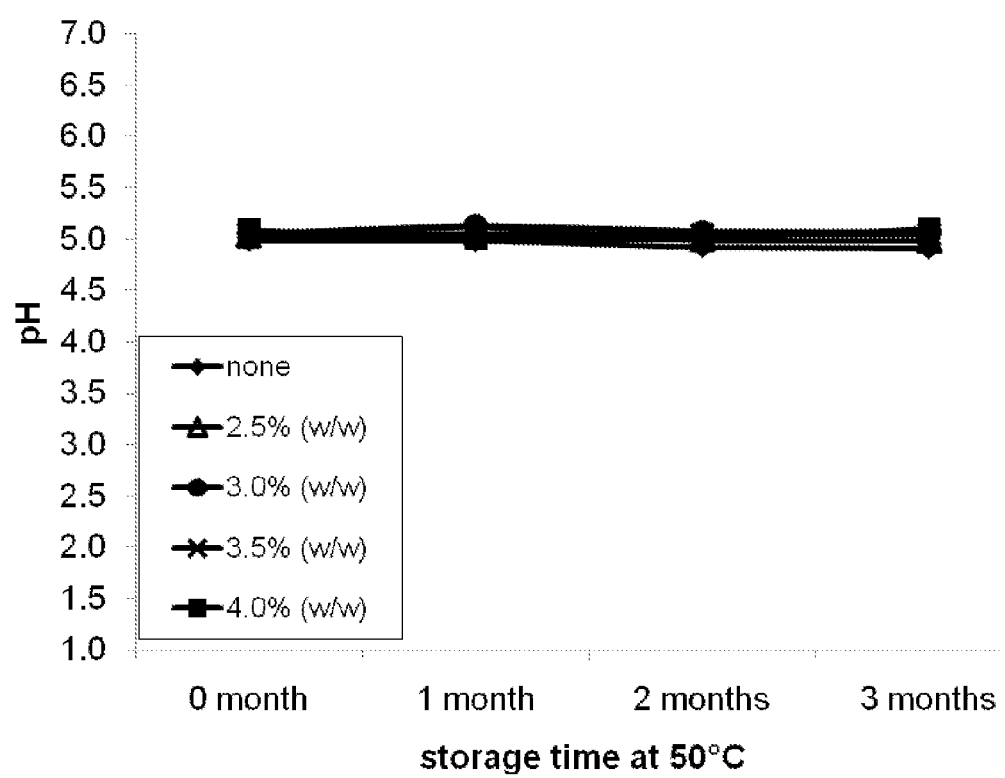
FIG. 15 is a graph of hydrogen peroxide pH as a function of storage time at 50° C. for samples produced in accordance with Example 3.
Figure 16:
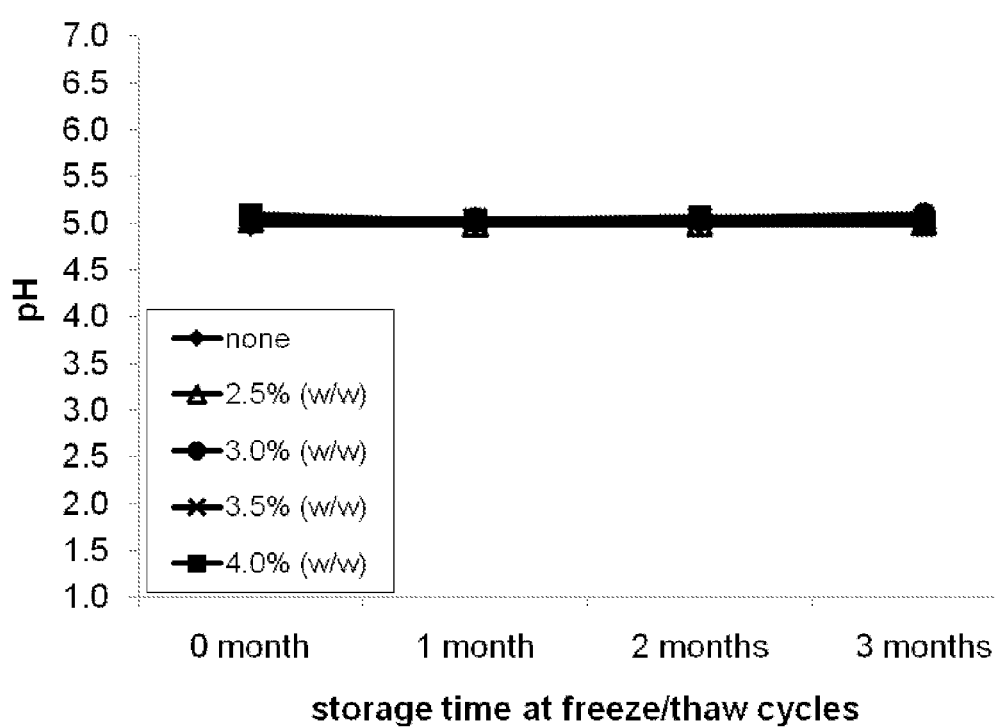
FIG. 16 is a graph of hydrogen peroxide pH as a function of storage time at freeze/thaw cycles for samples produced in accordance with Example 3.
Figure 17:
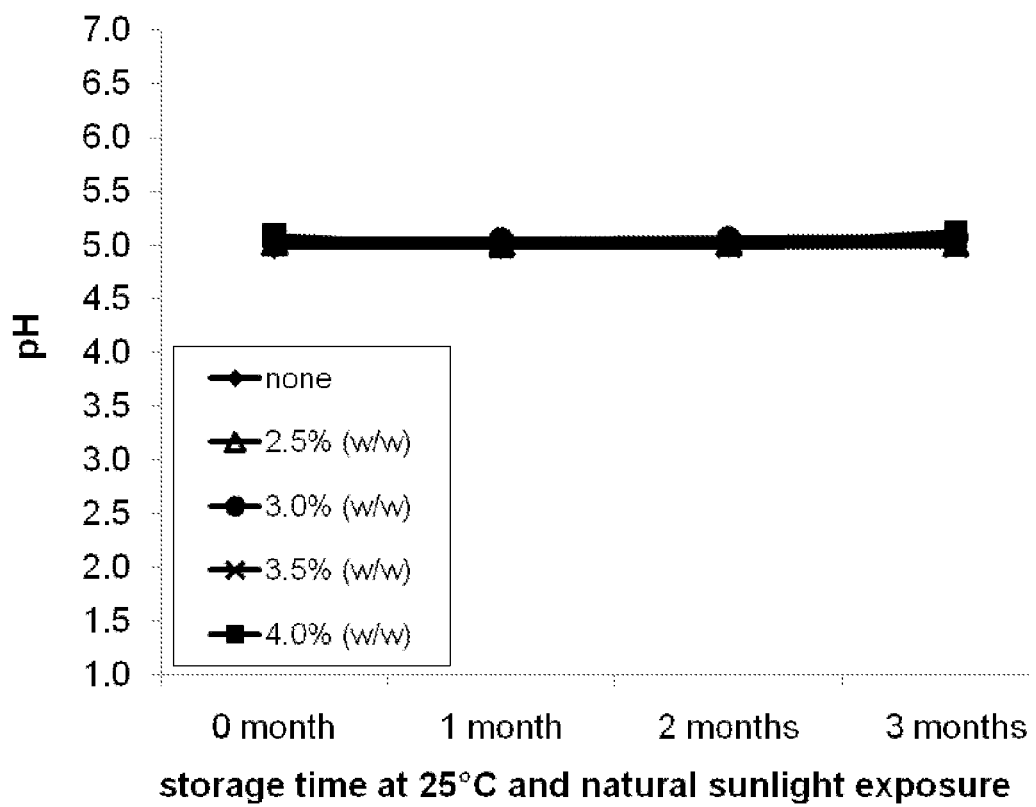
FIG. 17 is a graph of hydrogen peroxide pH as a function of storage time at 25° C. and exposed to natural sunlight for samples produced in accordance with Example 3.

The present application relates to new and surprisingly versatile thickened compositions that find usefulness in changing the color of keratin fibers (like hair), compositions that are known in the art as color bases, developers, color mixes, and hair color products. These traditionally difficult-to-thicken compositions are surprisingly thickened with the addition of lightly- to moderately-crosslinked poly(N-vinyl-2-pyrrolidone (PVP) when added to either the color base, the developer, or both the color base and the developer. Additionally, the application provides a method for coloring keratin fibers wherein the color mix is thickened with lightly- to moderately-crosslinked PVP.

Also provided is a method for coloring hair using the compositions of the present application. This method has advantages over known methods in terms of the ease of application and the colored hair attributes.

The reader will find the following definitions helpful before particular embodiments are described.

The term color base, also known as color blend (not to be confused with color mix, the definition of which follows), oxidative dye base or simply as dye base, refers to any composition having dye and/or dye precursor(s) that contribute, in part, to impart a color effect of keratin fibers.

The term developer, also known as oxidizer, refers to any composition having an oxidizing agent. Commonly encountered oxidizers used to treat keratin fibers include hydrogen peroxide, sodium perborate, monoethanolamine, 2-amino-2-methylpropanol, sodium carbonate, and/or urea peroxide.

The term color mix refers to the hair color composition that is applied to hair. Typically, the color mix is derived from two or more parts that are mixed together, such as the color base and the developer, although one-part color mixes are known to one skilled in the art and are included in the invention. Examples of one-part color mixes include temporary and semi-permanent color mixes.

The term hair color product refers to any number of consumer products sold for the purpose of altering, changing, highlighting or otherwise modifying the natural hair color of a subject. Hair color products may be sold as a kit containing only one part (especially for temporary and semi-permanent color mixes), but more typically contain two or more parts that are mixed together prior to application. The two or more parts are usually at least one color base and at least one developer. Other parts may include color or hue enhancers, and conditioners.

The term lightly- to moderately-crosslinked PVP, unless otherwise noted, specifically refers to polymer essentially consisting of lightly- to moderately-crosslinked poly(N-vinyl-2-pyrrolidone) having at least one of the following characteristics: (1) an aqueous swelling parameter defined by its gel volume from about 15 mL/g to about 300 mL/g, more preferably from about 15 mL/g to about 250 mL/g, and most preferably from about 15 mL/g to about 150 mL/g, or (2) a Brookfield viscosity of 5% lightly- to moderately-crosslinked PVP in a liquid carrier comprising water at 25° C. of at least 2,000 cP, more preferably of at least about 5,000 cP, and most preferably of at least about 10,000 cP. Disclosure for these parameter ranges is provided in U.S. Pat. No. 5,073,614 and in Shih, J. S., et al. (1995). Synthesis methods for the lightly- to moderately-crosslinked PVP are disclosed in a number of references, including U.S. Pat. Nos. 5,073,614; 5,654,385; and 6,177,068. It is appreciated by a polymer scientist skilled in the art that the method of synthesis is immaterial, inasmuch as the produced polymer achieves at least one of the above-defined parameters.

For example, U.S. Pat. No. '614 discloses different crosslinkers and crosslinker amounts that yield lightly- to moderately-crosslinked PVP suitable for the present invention. The effect of crosslinker amount on swell volume and viscosity is graphically presented in Shih, J. S., et al. (1995). Thus, the lightly- to moderately-crosslinked PVP may be produced by the precipitation polymerization method of the '614 patent, by the hydrogel method described in the '385 patent, or by the non-aqueous, heterogeneous polymerization method of the '068 patent. Certainly, other techniques are contemplated to synthesize this polymer, provided the product meets the aqueous swelling parameter and Brookfield viscosity requirements.

Final product viscosities may slightly vary for compositions containing lightly- to moderately-crosslinked PVP made by these different methods. Nonetheless, these variations are within the scope of the invention, as the lightly- to moderately-crosslinked PVPs thickens the color base and/or developer and/or color mix.

Unless otherwise specified, the term lightly- to moderately-crosslinked PVP does not refer to swellable but water-insoluble crosslinked PVP, such as the type sold into commercial trade under the trade name Polyclar® by International Specialty Products, which differs from the abovedescribed lightly- to moderately-crosslinked PVP.

The term viscosity refers to the proportionality coefficient between shear stress and shear rate, and describes a composition's resistance to flow. Because viscosity is dependent on shear rate, specific measurement information (such as viscometer, flow apparatus/spindle, and shear rate) is required to properly define viscosity. As used herein, viscosity refers to the proportionality coefficient determined from low shear rate, rotational flow, especially the viscosity measured by the Brookfield LVT and Brookfield RVT viscometers operating at 10 revolutions per minute (rpm) at 25° C. References describing the Brookfield measurement of viscosities include the following, each of which is hereby incorporated in its entirety by reference: Thibodeau, L., "Measuring viscosity of pastes," American Laboratory News, June 2004; McGregor, R. G., "Shelf life: does viscosity matter?" Pharmaceutical Online, Oct. 31, 2007; and McGregor, R. G., "When ointments disappoint, the viscosity story," Brookfield Engineering brochure.

Thickened Color Bases, Thickened Developers, Thickened Color Mixes

Unexpectedly, the inventors of the current discovery found that the addition of lightly- to moderately-crosslinked PVP effectively thickens compositions used to color keratin fibers, such as hair or wool. The discovery was surprising for several reason, including the increase in viscosity imparted to these difficult-to-thicken compositions, and the formulation versatility the approach offers. With the addition of up to 5% (w/w) lightly- to moderately-crosslinked PVP, viscosities suitable for color mixes were attained. Surprisingly, this polymer can be added to either the color base or the developer, and yield effectively thickened color mixes. Not only does this level of thickening resolve the challenging problem for these compositions, but it also provides the formulation scientist another route for developing hair color compositions, that is, the invention provides formulation flexibility.

Lightly- to moderately-crosslinked PVP also can be added to one-part hair coloring systems (e.g., wherein the color base and developer are provided pre-blended and ready for use without mixing) and attain similar benefits described for color mixes derived from blending two or more parts.

In one embodiment, lightly- to moderately-crosslinked PVP is added to the color base at an addition level up to 10% (w/w), based on the total weight of the color base. It may be preferred to use a high-speed homogenizer (such as a Greerco or Silverson high-shear mixer) in the production of the thickened color base to ensure its uniformity. At these addition levels the color base typically has a viscosity from about 50 cP to 100,000 cP or even more. More typically, suitable addition levels of the lightly- to moderately-crosslinked PVP to the color base are up to 5% (w/w), based on the total weight of the color base. The formulation scientist skilled in hair colors understands how to add the polymer, blend and homogenize with co-ingredients to obtain a uniform color base, and then test the Brookfield viscosity to determine if the addition level of lightly- to moderately-crosslinked PVP is satisfactory.

As illustrated in Example 1, viscosities ranging from 8,700 cP to 53,000 cP were measured for three popular, commercially-available color mixes when 3% (w/w color base) lightly- to moderately-crosslinked PVP was added to the color base. Neither the thickened color base nor the color mix exhibited the stringiness, fish eyes, or product non-uniformity noted with other thickeners. When this polymer was added at 5% (w/w) addition level to the color base, color mix viscosities ranged from 15,900 cP to 65,600 cP. The thickened color base and the final color mix exhibited the uniformity, texture, and workability qualities desired for applying to keratin fibers.

A different embodiment of the invention provides for thickened color mixes wherein the lightly- to moderately-crosslinked PVP is added to the developer part. The amount of lightly- to moderately-crosslinked PVP added to the developer part may range up to 10% (w/w), based on the total weight of the developer. Again, a skilled formulation scientist understand how to determine the appropriate amount of this polymer to attain satisfactory viscosity and performance results.

As hydrogen peroxide-based developers predominate in commercial formulas, a generic developer, being 6% hydrogen peroxide aqueous solution, was selected to illustrate this aspect of the invention. Then, this thickened, generic developer was blended with three commercial color bases. In general, color mix viscosities were lower using this approach. Nonetheless, color bases of 500 cP or more were produced with 2.5% (w/w developer), and a product that does not run or drip was formulated.

It is noted that hair color developers are known that contain more than 6% hydrogen peroxide. For example, WO 2010/023560 teaches a lifting composition having 12.0% hydrogen peroxide that is suitable for use in hair colors. This patent application also teaches other oxidizers other than hydrogen peroxide, such as potassium persulfate, sodium persulfate, ammonium persulfate, and combinations thereof. This '560 patent application is incorporated herein its entirety by reference.

Thus, based on formulation and addition level of the lightly- to moderately-crosslinked PVP, preferred color bases and developers of the invention exhibit a Brookfield viscosity from about 500 cP to about 100,000 cP when measured at 25° C. at 10 rpm using an appropriate spindle for the viscometer. Given consumer preferences for thickness and ease of blending, more preferred color bases and developers of the invention exhibit a viscosity from about 1,000 cP to about 50,000 cP.

Once blended, the at least one color base and the at least one developer are blended together create the color mix, which is applied to keratin fibers such as hair. Much of the final viscosity of this color mix depends on the color base and developer formulations, which in turn, can depend on the addition amount of lightly- to moderately-crosslinked PVP. Generally speaking, the color mix will resemble a thickened liquid, a flowable/spreadable gel, or a workable paste with a Brookfield viscosity from about 1,000 cP to 100,000 cP when measured at 25° C. and 10 rpm using an appropriate spindle. Consumer preferences may dictate a narrower range in viscosity from about 1,000 cP to 15,000 cP to avoid dripping and running while still enabling ease of blending and application. If a thickened color mix viscosity is deemed too high, then reductions can be made in the amount of lightly- to moderately-crosslinked PVP or other thickener(s) that may be present in the color base, the developer, or in both parts. This decrease in thickener(s) may be advantageous to remove potential formulation incompatibility(ies), enable new materials to be added into the formula, and/or reduce cost.

Viscosity Synergy

In another embodiment of the invention, the present application also provides for compositions exhibiting an unexpected build in viscosity. The magnitude of this thickening can be more than just the linear addition of the lightly- to moderately-crosslinked PVP in water alone. Without being bound by theory, this effect is believed to be of the associative thickening type, wherein a interactive complexation is created between the lightly- to moderately-crosslinked PVP and one or more ingredients present in the color base, the developer, or in one-part color mixes.

Consider an aqueous solution of 3% lightly- to moderately-crosslinked PVP, which has a viscosity of +2,300 cP (Shih, J., et al., "Characteristics of lightly crosslinked poly(N-vinylpyrrolidone)," Polymer Materials: Science & Engineering, 72, 374, 1995). Yet, when an identical amount of this polymer is added to a commercial hair color base (as detailed in Example 1), the change in viscosity ($\Delta\eta$) is not +2,300 cP, but an astonishing $\Delta\eta$=+81,800 cP.

In another embodiment, the associative thickening effect is pronounced in the blended color mix, even though an increase in viscosity is not measured for the color base or developer part. Example 1 also illustrates commercial hair colors #1 and #3 wherein the color base was effectively thickened with 3% lightly- to moderately-crosslinked PVP, but to an amount less than 2,300 cP (the viscosity of the polymer in water). A very significant synergy in thickening was discovered after blending these thickened color bases with their corresponding, commercially-supplied developers to create the color mixes. For commercial hair color #1 the increase in color mix viscosity was $\Delta\eta$=+45,070 cP, and for commercial hair color #3 an increase of $\Delta\eta$=+22,800 cP was measured.

The cause of this viscosity synergy is believed to be an interaction between the lightly- to moderately-crosslinked PVP and one or more ingredients in the commercial products. More specifically, alcohols, acids, and surfactants appear to provide favorable complexation with the polymer to increase the viscosity of the color base, the developer, and the color mix. A brief description of each of these ingredient categories is provided to acquaint the reader with preferred examples of each.

Viscosity Synergist: Alcohols

As used herein, the term alcohol refers to any molecule having at least one hydroxyl (—OH) functional group. These alcohols may exist in the liquid or solid state. There are several classifications of alcohols that find utility in the invention, each of which is considered separately.

In the first such category, the alcohol is a simple alcohol, meaning that it comprises only one hydroxyl group. Examples of preferred simple alcohols include ethanol, 1-propanol, and 2-propanol. Alcohols like these may provide an added benefit by serving as a carrier or solvent in the color base, developer, and/or color mix. Also preferred, the simple alcohol may be a saturated or unsaturated fatty alcohol having from between 8 to 34 carbon atoms amongst the carbon chain. Fatty alcohols are common components to hair color compositions where they may function as a surfactant, emulsifier, emollient, and/or thickener. Especially preferred fatty alcohols that can provide effective associative thickening complexation with lightly- to moderately-crosslinked PVP include the following: oleyl alcohol, cetearyl alcohol, capryl alcohol, 2-ethylhexyl alcohol, pelargonic alcohol, capric alcohol, lauryl alcohol, myristyl alcohol, cetyl alcohol, stearyl alcohol, elaidyl alcohol, linoleyl alcohol, elaidolinolenyl alcohol, ricinoleyl alcohol, nonadecyl alcohol, arachidyl alcohol, behenyl alcohol, ceryl alcohol, montanyl alcohol, myricyl alcohol, geddyl alcohol, and cetearyl alcohol. Highly preferred are fatty alcohols are those having from 8 to 22 carbon atoms.

Polyols are another type of alcohol finding utility for its associative properties. Unlike their simple alcohol counterparts, polyols are compounds having more than one hydroxyl group. Polyols that exhibit a viscosity synergy with lightly- to moderately-crosslinked PVP include, without limitation: propylene glycol, glycerin, butylene glycol, hexylene glycol, and sorbitol.

Viscosity Synergist: Acids

Acids also can confer a thickening effect when added to lightly- to moderately-crosslinked PVP in the color base, developer, and/or color mix. Preferred acids are organic acids having one or more carboxyl, sulfonyl, groups, and/or thionyl groups. Preferred acids include the acids of each saturated and unsaturated fatty alcohol listed earlier, such as: oleyl acid, capryl acid, 2-ethylhexyl acid, pelargonic acid, capric acid, lauric acid, myristic acid, cetylic (palmitic) acid, stearic acid, elaidic acid, linoleic acid, octadecadienoic acid, ricinoleic (ricinic) acid, nonadecylic acid, arachidonic acid, behenolic acid, cerotic (ceric) acid, montanic acid, myricic acid, and geddic acid.

Viscosity Synergist: Surfactants

Surfactants also display a synergistic interaction with lightly- to moderately-crosslinked PVP to increase viscosity. Surfactants suitable for use in the present invention include those selected from the anionic, cationic, amphoteric (also called zwitterionic), and non-ionic families of surfactants, and blends thereof.

Anionic surfactants include alkyl sulfate, alkyl ethoxylated sulfate, and mixtures thereof. These materials have the respective formula (1) $ROSO_3M$ and (2) $RO(C_2H_4O)_xSO_3M$, wherein R is alkyl or alkenyl of from about 8 to about 30 carbon atoms, x is 1 to 10, and M is H or a salt-forming cation such as ammonium, alkanolamine containing C1-C3 alkyl groups such as triethanolamine, and monovalent and polyvalent metals such as the alkaline and alkaline earth metals. Preferred metals include sodium, potassium, magnesium, and calcium. The cation M, of the anionic surfactant should preferably be chosen such that the anionic surfactant component is water soluble. Solubility of anionic surfactants, in general, will depend upon the particular anionic surfactants and cations chosen. It is preferred that the anionic surfactant be soluble in the composition hereof.

Preferably, R has from about 10 to about 18 carbon atoms in both the alkyl and alkyl ethoxylated sulfates. The alkyl ethoxylated sulfates are typically made as condensation products of ethylene oxide and monohydric alcohols having from about 8 to about 24 carbon atoms. The alcohols can be derived from fats, e.g., coconut oil, palm kernel oil, or tallow, or can be synthetic. Such alcohols are preferably reacted with about 1 to about 10, more preferably from about 1 to about 4, most preferably from about 2 to about 3.5, molar proportions of ethylene oxide and the resulting mixture of molecular species having, for example, an average of 3 moles of ethylene oxide per mole of alcohol, is sulfated and neutralized.

Specific examples of alkyl ether sulfates which may be used in the present invention are sodium and ammonium salts of coconut alkyl triethylene glycol ether sulfate; tallow alkyl triethylene glycol ether sulfate, and tallow alkyl hexaoxyethylene sulfate. Highly preferred alkyl ether sulfates are those comprising a mixture of individual compounds, said mixture having an average alkyl chain length of from about 12 to about 16 carbon atoms and an average degree of ethoxylation of from about 1 to about 4 moles of ethylene oxide. The sulfate surfactant is preferably comprised of a combination of ethoxylated and nonethoxylated sulfates. Alkyl sulfates can provide excellent cleaning and lather performance. Alkyl ethoxylated sulfates can provide excellent cleaning performance.

Other suitable anionic detersive surfactants include, but are not limited to water-soluble salts of organic, sulfuric acid reaction products of the general formula $R_1SO_3M$ where $R_1$ is selected from the group consisting of a straight or branched chain, saturated aliphatic hydrocarbon radical having from about 8 to about 24, preferably about 10 to about 18, carbon atoms; and M is a cation such as ammonium, alkanolamines, such as triethanolamine, monovalent metals, such as sodium and potassium, and polyvalent metal cations, such as magnesium, and calcium. The cation M, of the anionic detersive surfactant should be chosen such that the detersive surfactant component is water soluble. Solubility will depend upon the particular anionic detersive surfactants and cations chosen. Examples of such detersive surfactants are the salts of an organic sulfuric acid reaction product of a hydrocarbon of the methane series, including iso and n-paraffins, having about 8 to about 24 carbon atoms, preferably about 10 to about 18 carbon atoms and a sulfonating agent, e.g., $SO_3$, $H_2SO_4$, obtained according to known sulfonation methods, including bleaching and hydrolysis. Preferred are alkali metal and ammonium sulfonated C10-C18 n-paraffins.

Suitable classes of nonionic surfactants also include, but are not limited to:

1. The polyethylene oxide condensates of alkyl phenols, e.g., the condensation products of alkyl phenols having an alkyl group containing from about 6 to about 12 carbon atoms in either a straight chain or branched chain configuration, with ethylene oxide, the said ethylene oxide being present in amounts equal to from about 10 to about 60 moles of ethylene oxide per mole of alkyl phenol. The alkyl substituent in such compounds may be derived from polymerized propylene, diisobutylene, octane, or nonane, for example.
2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of about 2,500 to about 3,000, are satisfactory.
3. The condensation product of aliphatic alcohols having from about 8 to about 18 carbon atoms, in either straight chain or branched chain configuration, with ethylene oxide, e.g., a coconut alcohol ethylene oxide condensate having from about 10 to about 30 moles of ethylene oxide per mole of coconut alcohol, the coconut alcohol fraction having from about 10 to about 14 carbon atoms.
4. Long chain tertiary amine oxides corresponding to the following general formula: $R_1R_2R_3N \rightarrow O$, wherein $R_1$ contains an alkyl, alkenyl or monohydroxy alkyl radical of from about 8 to about 18 carbon atoms, from 0 to about 10 ethylene oxide moieties, and from 0 to about 1 glyceryl moiety, and $R_2$ and $R_3$ contain from about 1 to about 3 carbon atoms and from 0 to about 1 hydroxy group, e.g., methyl, ethyl, propyl, hydroxyethyl, or hydroxypropyl radicals. The arrow in the formula is a conventional representation of a semipolar bond. Non-limiting examples of amine oxides suitable for use in this invention include dimethyl-dodecylamine oxide, dimethyloctylamine oxide, dimethyl-decylamine oxide, dimethyl-tetradecylamine oxide, 3,6,9-tri-oxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl) amine oxide, dimethylhexadecylamine oxide.

5. Long chain tertiary phosphine oxides corresponding to the following general formula: RR'R"P→O wherein R contains an alkyl, alkenyl or monohydroxyalkyl radical ranging from about 8 to about 18 carbon atoms in chain length, from 0 to about 10 ethylene oxide moieties and from 0 to about 1 glyceryl moiety and R' and R" are each alkyl or monohydroxyalkyl groups containing from about 1 to about 3 carbon atoms. The arrow in the formula is a conventional representation of a semipolar bond. Examples of suitable phosphine oxides include, but are not limited to: dodecyldimethylphosphine oxide, tetradecyldimethylphosphine oxide, tetradecylmethylethylphosphine oxide, 3,6,9,-trioxaoctadecyldimethylphosphine oxide, cetyidimethylphosphine oxide, 3-dodecoxy-2-hydroxypropyldi(2-hydroxyethyl) phosphine oxide, stearyldimethylphosphine oxide, cetylethylpropylphosphine oxide, oleyldiethylphosphine oxide, dodecyldiethylphosphine oxide, tetradecyldiethylphosphine oxide, dodecyldipropylphosphine oxide, dodecyldi(hydroxymethyl)phosphine oxide, dodecyldi(2-hydroxyethyl)phosphine oxide, tetradecylmethyl-2-hydroxypropylphosphine oxide, oleydimethylphosphine oxide, 2-hydroxydodecyldimethylphosphine oxide.

6. Long chain dialkyl sulfoxides containing one short chain alkyl or hydroxy alkyl radical of from about 1 to about 3 carbon atoms (usually methyl) and one long hydrophobic chain which include alkyl, alkenyl, hydroxy alkyl, or keto alkyl radicals containing from about 8 to about 20 carbon atoms, from 0 to about 10 ethylene oxide moieties and from 0 to about 1 glyceryl moiety. Examples include, but are not limited to: octadecyl methyl sulfoxide, 2-ketotridecyl methyl sulfoxide, 3,6,9,-trixaoctadecyl 2-hydroxyethyl sulfoxide, dodecyl methyl sulfoxide, oleyl 3-hydroxypropyl sulfoxide, tetradecyl methyl sulfoxide, 3-methoxytridecyl methyl sulfoxide, 3-hydroxytridecyl methyl sulfoxide, 3-hydroxy-4-dodecoxybutyl methyl sulfoxide.

7. Polyalkylene oxide modified dimethylpolysiloxanes, also known as dimethicone copolyols. These materials include the polyalkylene oxide modified dimethylpolysiloxanes of the following formulae:

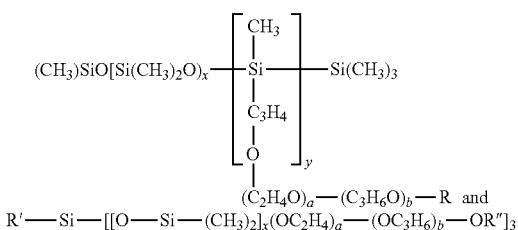

wherein R is hydrogen, an alkyl group having from 1 to about 12 carbon atoms, an alkoxy group having from 1 to about 6 carbon atoms or a hydroxyl group; R' and R" are alkyl groups having from 1 to about 12 carbon atoms; x is an integer of from 1 to 100, preferably from 20 to 30; y is an integer of 1 to 20, preferably from 2 to 10; and a and b are integers of from 0 to 50, preferably from 20 to 30. Dimethicone copolyols among those useful herein are disclosed in the following patent documents: U.S. Pat. Nos. 4,122,029; 4,265,878; and 4,421,769. Commercially available dimethicone copolyols, useful herein, include Silwet Surface Active Copolymers (manufactured by the Union Carbide Corporation); Dow Corning Silicone Surfactants (manufactured by the Dow Corning Corporation); Silicone Copolymer F-754 (manufactured by SWS Silicones Corp.); and Rhodorsil 70646 Fluid (manufactured by Rhone Poulenc, Inc.).

Specifically, anionic surfactants for use in the invention include: ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, and combinations thereof.

Surfactant systems useful in the present invention may also comprise cationic surfactants. Cationic surfactants typically contain amino or quaternary ammonium hydrophilic moieties which are positively charged when dissolved in the aqueous composition of the present invention. Cationic surfactants among those useful herein are disclosed in the following documents: McCutcheon's, Detergents & Emulsifiers, (M.C. Publishing Co., North American edition 1989); Schwartz, et al., Surface Active Agents, Their Chemistry and Technology. New York: Interscience Publishers, 1949; U.S. Pat. Nos. 3,155,591; 3,929,678; 3,959,461; and 4,387,090.

Among the quaternary ammonium-containing cationic surfactant materials useful herein are those of the general formula:

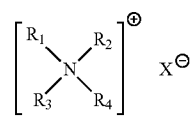

wherein $R_1$-$R_4$ are independently an aliphatic group of from about 1 to about 22 carbon atoms, or an aromatic, alkoxy, polyoxyalkylene, alkylamido, hydroxyalkyl, aryl or alkylaryl group having from about 12 to about 22 carbon atoms; and X is an anion selected from halogen, acetate, phosphate, nitrate and alkylsulfate radicals. The aliphatic groups may contain, in addition to carbon and hydrogen atoms, ether linkages, and other groups such as amino groups.

Other quaternary ammonium salts useful herein have the formula:

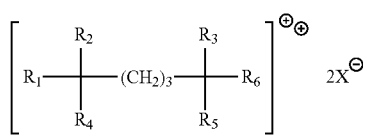

wherein $R_1$ is an aliphatic group having from about 16 to about 22 carbon atoms, $R_2$, $R_3$, $R_4$, $R_5$, and $R_6$ are selected from hydrogen and alkyl having from about 1 to about 4 carbon atoms, and X is an ion selected from halogen, acetate, phosphate, nitrate and alkyl sulfate radicals. Such quaternary ammonium salts include tallow propane diammonium dichloride.

Quaternary ammonium salts include monoalkyltrimethylammonium chlorides and dialkyldimethylammonium chlorides and trialkyl methyl ammonium chlorides, wherein at least one of the alkyl groups have from about 12 to about 22 carbon atoms and are derived from long-chain fatty acids, such as hydrogenated tallow fatty acid (tallow fatty acids yield quaternary compounds wherein the long chain alkyl groups are predominately from 16 to 18 carbon atoms). Examples of quaternary ammonium salts useful in the present invention include, but are not limited to, stearyl trimethyl ammonium chloride, ditallowedimethyl ammonium chloride, ditallowedimethyl ammonium methyl sulfate, dihexadecyl dimethyl ammonium chloride, di(hydrogenated tallow) dimethyl ammonium chloride, dioctadecyl dimethyl ammonium chloride, dieicosyl dimethyl ammonium chloride, didocosyl dimethyl ammonium chloride, di(hydrogenated tallow)dimethyl ammonium acetate, dihexadecyl dimethyl ammonium chloride, dihexadecyl dimethyl ammonium acetate, ditallow dipropyl ammonium phosphate, ditallow dimethyl ammonium nitrate, di(coconutalkyl)dimethyl ammonium chloride, and stearyl dimethyl benzyl ammonium chloride, ditallow dimethyl ammonium chloride, dicetyl dimethyl ammonium chloride, stearyl dimethyl benzyl ammonium chloride and cetyl trimethyl ammonium chloride are preferred quaternary ammonium salts useful herein.

In addition to the abovedescribed anionic and cationic surfactants, amphoteric surfactant components useful in the present composition include those known to be useful in personal cleansing compositions. Examples of amphoteric surfactants suitable for use in the composition herein are described in U.S. Pat. No. 5,104,646 (Bolich Jr., et al.) and U.S. Pat. No. 5,106,609 (Bolich Jr., et al.). Examples of amphoteric detersive surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate.

Other amphoterics, sometimes classified as zwitterionics, such as betaines can also be used in the present invention. Such zwitterionics are considered as amphoterics in the present invention where the zwitterionic has an attached group that is anionic at the pH of the composition. Examples of betaines useful herein include the high alkyl betaines, such as. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the $RCONH(CH_2)_3$ radical is attached to the nitrogen atom of the betaine are also useful in this invention.

Specifically, examples of amphoteric surfactants for use in the invention include: coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl)carboxymethyl betaine, oleyl dimethyl gamma-carboxypropyl betaine, and lauryl bis-(2-hydroxypropyl)-α-carboxyethyl betaine. Other examples of amphoteric surfactants are sodium 3-dodecyl-aminopropionate, sodium 3-dodecylaminopropane sulfonate, sodium lauroamphoacetate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name Miranol™ and described in U.S. Pat. No. 2,528,378.

Experience has shown that customary addition levels of the alcohol, acid, and/or surfactant are sufficient to produce the combination viscosity benefit with lightly- to moderately-crosslinked PVP. That is, the preferred addition level of each alcohol, acid, or surfactant is from 0.1% (w/w) to 25% (w/w), and more preferably ranges from 1% (w/w) to 10% (w/w) to induce the viscosity enhancement. One skilled in the art understands the necessary steps needed to evaluate the most preferred addition level for a particular formulation.

One or more alcohol(s), acid(s), and surfactant(s) may be used, as well as combinations thereof.

Optional: Additional Formulation Ingredients and Adjuvants

Due to the requirements of end performance, it is expected that the compositions of this invention likely will be used together with other additives to further enhance the properties of the finished product. Such ingredients may be incorporated without altering the scope of the current invention.

These formulations inevitably have a liquid or liquid-like carrier that aides to distribute, disperse, and/or dissolve the formulation ingredients, including the lightly- to moderately-crosslinked PVP. Selection of these carriers is not limited, and examples of liquid carriers include water, alcohols, oils, esters, and blends thereof.

A preferred, optional ingredient is one or more color couplers. These oxidation dye precursors are colorless or weakly colored compounds which, when combined with one or more dyes and oxidizers, give rise to colored complexes by a process of oxidative condensation. Typical couplers include 1,2- and 1,3-disubstituted benzene derivatives. Polyhydric alcohols also are suitable couplers. Examples of couplers are provided in U.S. patent application 2008/0201870 and WO 2010/023560 (the contents of which are incorporated in their entirety by reference), and include resorcinol, 1-naphthol, phenyl methylpyrazolone, m-aminophenol, 4-amino-2-hydroxytoluene, 2-methylresorcinol, 1-naphthol, m-aminophenols, m-phenylenediamines and m-naphthols, mono- or polyhydroxylated naphthalene derivatives, and heterocyclic couplers such as, for example, indole derivatives, indoline derivatives, sesamol and its derivatives, pyridine derivatives, pyrazolotriazole derivatives, pyrazolones, indazoles, benzimidazoles, benzothiazoles, benzoxazoles, 1,3-benzodioxoles, quinolines, benzomorpholine derivatives, pyrazoloazole derivatives, pyrroloazole derivatives, imidazoloazole derivatives, pyrazolopyrimidine derivatives, pyrazoline-3,5-dione derivatives, pyrrolo[3,2-d]oxazole derivatives, pyrazolo[3,4-d]thiazole derivatives, thiazoloazole S-oxide derivatives, thiazoloazole S,S-dioxide derivatives, and the acid addition salts thereof.

Another source of representative dyes and couplers suitable for use in the present invention is found in Sagarin, "Cosmetic Science and Technology," Interscience, Special Ed., volume 2, pages 308 to 310, which is incorporated herein its entirety by reference.

It may be desirable to formulate the color base and/or the developer with one or more inert particles for the purpose of contributing to or enhancing the bleaching role traditionally served by the oxidizer (e.g., hydrogen peroxide) while reducing damage to the keratin fibers and skin irritation. Disclosure of these compositions is provided by U.S. Pat. No. 7,682,402, the contents of which are incorporated herein their entirety by reference. In this context, the term inert particle means any mineral, plant or synthetic particle that is insoluble in the medium, of any form, solid, hollow or porous, which is chemically inert with respect to the oxidizing agent. Examples of inert particles include coated and uncoated titanium oxides, zinc oxides, carbonates, silicates, sulfides, polyamides, polyesters, polystyrenes, polyurethanes, polycyanoacrylates, polyethylenes, polymethyl methacrylates, polypropylenes, polycarbonates, Teflon®, silicone resins, silicone elastomers, waxes and complex synthetic compounds, and combinations thereof. Lightly- to moderately-crosslinked PVP serves not only to thicken the color base, developer, and/or color mix, but also to suspend the inert particles to maximize their effectiveness.

The compositions of the invention also can contain one or more additional additives chosen from conditioning agents, protecting agents, such as, for example, hydrosoluble, anti-radical agents, antioxidants, vitamins and pro-vitamins, fixing agents, oxidizing agents, reducing agents, dyes, cleansing agents, anionic, cationic, nonionic and amphoteric surfactants, thickeners, perfumes, pearlizing agents, stabilizers, pH adjusters, filters, preservatives, cationic and nonionic polyether associative polyurethanes, polymers other than the cationic polymer described herein, vegetable oils, mineral oils, synthetic oils, polyols such as glycols and glycerol, silicones, aliphatic alcohols, colorants, bleaching agents, highlighting agents and sequestrants. These additives are present in the composition according to the invention in proportions that may range from 0% to 20% by weight in relation to the total weight of the composition. The precise amount of each additive may be easily determined by an expert in the field according to its nature and its function.

For example, the compositions according to the invention may be used to moisturize or retain moisture. Highly preferred are thickened formulations that are non-greasy, such as lotions having glycerin, caprylic/capric triglycerides, hydrogenated cocoglycerides, and/or one or more vegetable oils (e.g., *helianthus* oil, soybean oil, linseed oil, and olive oil).

Any known conditioning agent is useful in the personal care compositions of this invention. Conditioning agents function to improve the cosmetic properties of the hair, particularly softness, thickening, untangling, feel, and static electricity and may be in liquid, semi-solid, or solid form such as oils, waxes, or gums. Similarly, any known hair or skin altering agent is useful in the compositions of this invention. Preferred conditioning agents include cationic polymers, cationic surfactants and cationic silicones.

Conditioning agents may be chosen from synthesis oils, mineral oils, vegetable oils, fluorinated or perfluorinated oils, natural or synthetic waxes, silicones, cationic polymers, proteins and hydrolyzed proteins, ceramide type compounds, cationic surfactants, fatty amines, fatty acids and their derivatives, as well as mixtures of these different compounds.

The synthesis oils include polyolefins, e.g., poly-α-olefins such as polybutenes, polyisobutenes and polydecenes. The polyolefins can be hydrogenated.

The mineral oils suitable for use in the compositions of the invention include hexadecane and oil of paraffin.

A list of suitable animal and vegetable oils comprises sunflower, corn, soy, avocado, jojoba, squash, raisin seed, sesame seed, walnut oils, fish oils, glycerol tricaprocaprylate, Purcellin oil or liquid jojoba, and blends thereof.

Suitable natural or synthetic oils include eucalyptus, lavender, vetiver, litsea cubeba, lemon, sandalwood, rosemary, chamomile, savory, nutmeg, cinnamon, hyssop, caraway, orange, geranium, cade, and bergamot.

Suitable natural and synthetic waxes include carnauba wax, candelila wax, alfa wax, paraffin wax, ozokerite wax, vegetable waxes such as olive wax, rice wax, hydrogenated jojoba wax, absolute flower waxes such as black currant flower wax, animal waxes such as bees wax, modified bees wax (cerabellina), marine waxes and polyolefin waxes such as polyethylene wax, and blends thereof.

The cationic polymers that may be used as a conditioning agent according to the invention are those known to improve the cosmetic properties of hair treated by detergent compositions. The expression "cationic polymer" as used herein, indicates any polymer containing cationic groups and/or ionizable groups in cationic groups. The cationic polymers used generally have a molecular weight the average number of which falls between about 500 Da and 5,000,000 Da and preferably between 1000 Da and 3,000,000 Da.

The preferred cationic polymers are chosen from among those containing units including primary, secondary, tertiary, and/or quaternary amine groups that may either form part of the main polymer chain or a side chain.

Useful cationic polymers include known polyamine, polyaminoamide, and quaternary polyammonium types of polymers, such as:

(1) Homopolymers and copolymers derived from acrylic or methacrylic esters or amides. The copolymers can contain one or more units derived from acrylamides, methacrylamides, diacetone acrylamides, acrylamides and methacrylamides, acrylic or methacrylic acids or their esters, vinyllactams such as vinyl pyrrolidone or vinyl caprolactam, and vinyl esters. Specific examples include: copolymers of acrylamide and dimethyl amino ethyl methacrylate quaternized with dimethyl sulfate or with an alkyl halide; copolymers of acrylamide and methacryloyl oxyethyl trimethyl ammonium chloride; the copolymer of acrylamide and methacryloyl oxyethyl trimethyl ammonium methosulfate; copolymers of vinyl pyrrolidone/dialkylaminoalkyl acrylate or methacrylate, optionally quaternized, such as the products sold under the name Gafquat® by International Specialty Products; the dimethyl amino ethyl methacrylate/vinyl caprolactam/vinyl pyrrolidone terpolymers, such as the product sold under the name Gaffix® VC 713 by International Specialty Products; the vinyl pyrrolidone/methacrylamidopropyl dimethylamine copolymer, marketed under the name Styleze® CC 10 by International Specialty Products; the vinyl pyrrolidone/quaternized dimethyl amino propyl methacrylamide copolymers such as the product sold under the name Gafquat® HS 100 by International Specialty Products (Wayne, N.J.), and the terpolymer of N-vinyl-2-pyrrolidone, dimethylaminopropyl methacrylamide, and methacryloylaminopropyl lauryl dimethylammonium chloride, sold under the name Styleze® W, also by International Specialty Products.

(2) Derivatives of cellulose ethers containing quaternary ammonium groups, such as hydroxy ethyl cellulose quaternary ammonium that has reacted with an epoxide substituted by a trimethyl ammonium group.

(3) Derivatives of cationic cellulose such as cellulose copolymers or derivatives of cellulose grafted with a hydrosoluble quaternary ammonium monomer, as described in U.S. Pat. No. 4,131,576, such as the hydroxy alkyl cellulose, and the hydroxymethyl-, hydroxyethyl- or hydroxypropyl-cellulose grafted with a salt of methacryloyl ethyl trimethyl ammonium, methacrylamidopropyl trimethyl ammonium, or dimethyl diallyl ammonium.

(4) Cationic polysaccharides such as described in U.S. Pat. Nos. 3,589,578 and 4,031,307, guar gums containing cationic trialkyl ammonium groups and guar gums modified by a salt, e.g., chloride of 2,3-epoxy propyl trimethyl ammonium.

(5) Polymers composed of piperazinyl units and alkylene or hydroxy alkylene divalent radicals with straight or branched chains, possibly interrupted by atoms of oxygen, sulfur, nitrogen, or by aromatic or heterocyclic cycles, as well as the products of the oxidation and/or quaternization of such polymers.

(6) Water-soluble polyamino amides prepared by polycondensation of an acid compound with a polyamine. These polyamino amides may be reticulated.

(7) Derivatives of polyamino amides resulting from the condensation of polyalcoylene polyamines with polycarboxylic acids followed by alcoylation by bi-functional agents.

(8) Polymers obtained by reaction of a polyalkylene polyamine containing two primary amine groups and at least one secondary amine group with a dioxycarboxylic acid chosen from among diglycolic acid and saturated dicarboxylic aliphatic acids having 3 to 8 atoms of carbon. Such polymers are described in U.S. Pat. Nos. 3,227,615 and 2,961,347.

(9) Cyclopolymers of alkyl dialyl amine or dialkyl diallyl ammonium such as the homopolymer of dimethyl diallyl ammonium chloride and copolymers of diallyl dimethyl ammonium chloride and acrylamide.

(10) Quaternary diammonium polymers such as hexadimethrine chloride.

(11) Quaternary polyammonium polymers, including, for example, Mirapol® A 15, Mirapol® AD1, Mirapol® AZ1, and Mirapol® 175 products sold by Miranol.

(12) Quaternary polymers of vinyl pyrrolidone and vinyl imidazole such as the products sold under the names Luviquat® FC 905, FC 550, and FC 370 by BASF Corporation.

(13) Quaternary polyamines.

(14) Reticulated polymers known in the art.

Other cationic polymers that may be used within the context of the invention are cationic proteins or hydrolyzed cationic proteins, polyalkyleneimines such as polyethyleneimines, polymers containing vinyl pyridine or vinyl pyridinium units, condensates of polyamines and epichlorhydrins, quaternary polyurethanes, and derivatives of chitin.

Preferred cationic polymers are derivatives of quaternary cellulose ethers, the homopolymers and copolymers of dimethyl diallyl ammonium chloride, quaternary polymers of vinyl pyrrolidone and vinyl imidazole, and mixtures thereof.

The conditioning agent can be any silicone known by those skilled in the art to be useful as a conditioning agent. The silicones suitable for use according to the invention include polyorganosiloxanes that are insoluble in the composition. The silicones may be present in the form of oils, waxes, resins, or gums. They may be volatile or non-volatile. The silicones can be selected from polyalkyl siloxanes, polyaryl siloxanes, polyalkyl aryl siloxanes, silicone gums and resins, and polyorgano siloxanes modified by organofunctional groups, and mixtures thereof.

Suitable polyalkyl siloxanes include polydimethyl siloxanes with terminal trimethyl silyl groups or terminal dimethyl silanol groups (dimethiconol) and polyalkyl (C1-C20) siloxanes.

Suitable polyalkyl aryl siloxanes include polydimethyl methyl phenyl siloxanes and polydimethyl diphenyl siloxanes, linear or branched.

The silicone gums suitable for use herein include polydiorganosiloxanes preferably having a number-average molecular weight between 200,000 Da and 1,000,000, Da used alone or mixed with a solvent. Examples include polymethyl siloxane, polydimethyl siloxane/methyl vinyl siloxane gums, polydimethyl siloxane/diphenyl siloxane, polydimethyl siloxane/phenyl methyl siloxane and polydimethyl siloxane/diphenyl siloxane/methyl vinyl siloxane.

Suitable silicone resins include silicones with a dimethyl/trimethyl siloxane structure and resins of the trimethyl siloxysilicate type.

The organo-modified silicones suitable for use in the invention include silicones such as those previously defined and containing one or more organofunctional groups attached by means of a hydrocarbon radical and grafted siliconated polymers. Particularly preferred are amino functional silicones.

The silicones may be used in the form of emulsions, nanoemulsions, or micro-emulsions.

The conditioning agent can be a protein or hydrolyzed cationic or non-cationic protein. Examples of these compounds include hydrolyzed collagens having triethyl ammonium groups, hydrolyzed collagens having trimethyl ammonium and trimethyl stearyl ammonium chloride groups, hydrolyzed animal proteins having trimethyl benzyl ammonium groups (benzyltrimonium hydrolyzed animal protein), hydrolyzed proteins having groups of quaternary ammonium on the polypeptide chain, including at least one C1-C18 alkyl.

Hydrolyzed proteins include Croquat L, in which the quaternary ammonium groups include a C12 alkyl group, Croquat M, in which the quaternary ammonium groups include C10-C18 alkyl groups, Croquat S in which the quaternary ammonium groups include a C18 alkyl group and Crotein Q in which the quaternary ammonium groups include at least one C1-C18 alkyl group. These products are sold by Croda.

The conditioning agent can comprise quaternized vegetable proteins such as wheat, corn, or soy proteins such as cocodimonium hydrolyzed wheat protein, laurdimonium hydrolyzed wheat protein and steardimonium hydrolyzed wheat protein, 2-N-stearoyl amino-octadecane-1,3-diol, 2-N-behenoyl amino-octadecane-1,3-diol, 2-N-[2-hydroxypalmitoyl]-amino-octadecane-1,3-diol, 2-N-stearoyl amino-octadecane-1,3,4-triol, N-stearoyl phytosphingosine, 2-N-palmitoyl amino-hexadecane-1,3-diol, bis-(N-hydroxy ethyl N-cetyl)malonamide, N-(2-hydroxy ethyl)-N-(3-cetoxyl-2-hydroxy propyl)amide of cetylic acid, N-docosanoyl N-methyl-D-glucamine and mixtures of such compounds.

The conditioning agent can be a cationic surfactant such as a salt of a primary, secondary, or tertiary fatty amine, optionally polyoxyalkylenated, a quaternary ammonium salt, a derivative of imadazoline, or an amine oxide. Suitable examples include mono-, di-, or tri-alkyl quaternary ammonium compounds with a counterion such as a chloride, methosulfate, tosylate, etc. including, but not limited to, cetrimonium chloride, dicetyldimonium chloride, behentrimonium methosulfate, and the like. The presence of a quaternary ammonium compound in conjunction with the polymer described above reduces static and enhances combing of hair in the dry state. The polymer also enhances the deposition of the quaternary ammonium compound onto the hair substrate thus enhancing the conditioning effect of hair.

The conditioning agent can be any fatty amine known to be useful as a conditioning agent; e.g. dodecyl, cetyl or stearyl amines, such as stearamidopropyl dimethylamine.

The conditioning agent can be a fatty acid or derivatives thereof known to be useful as conditioning agents. Suitable fatty acids include myristic acid, palmitic acid, stearic acid, behenic acid, oleic acid, linoleic acid, and isostearic acid. The derivatives of fatty acids include carboxylic ester acids including mono-, di-, tri- and tetra-carboxylic acids.

The conditioning agent can be a fluorinated or perfluorinated oil. The fluoridated oils may also be fluorocarbons such as fluoramines, e.g., perfluorotributylamine, fluoridated hydrocarbons, such as perfluorodecahydronaphthalene, fluoroesters, and fluoroethers.

Of course, mixtures of two or more conditioning agents can be used.

The conditioning agent or agents can be present in an amount of 0.001% to 20%, preferably from 0.01% to 10%, and even more preferably from 0.1% to 3% by weight based on the total weight of the final composition.

The antioxidants or antiradical agents can be selected from phenols such as BHA (tert-butyl-4-hydroxy anisole), BHT (2,6-di-tert-butyl-p-cresol), TBHQ (tert-butyl hydroquinone), polyphenols such as proanthocyanodic oligomers, flavonoids, hindered amines such as tetra amino piperidine, erythorbic acid, polyamines such as spermine, cysteine, glutathione, superoxide dismutase, and lactoferrin.

The vitamins can be selected from ascorbic acid (vitamin C), vitamin E, vitamin E acetate, vitamin E phosphate, B vitamins such as B3 and B5, niacin, vitamin A, and derivatives thereof. The provitamins can be selected from panthenol and retinol.

The protecting agent can be present in an amount 0.001% to 20% by weight, preferably from 0.01% to 10% by weight, and more preferably 0.1 to 5% by weight of the total weight of the final composition.

In addition, the compositions according to the invention advantageously include at least one surfactant, which can be present in an amount of 0.1% and 60% preferably 1% and 40%, and more preferably 5% and 30% by weight based on the total weight of the composition. The surfactant may be chosen from among anionic, amphoteric, or non-ionic surfactants, or mixtures of them known to be useful in personal care compositions.

Additional thickeners or viscosity increasing agents may be included in the composition of the invention, such as: Acetamide MEA; acrylamide/ethalkonium chloride acrylate copolymer; acrylamide/ethyltrimonium chloride acrylate/ ethalkonium chloride acrylate copolymer; acrylamides copolymer; acrylamide/sodium acrylate copolymer; acrylamide/sodium acryloyldimethyltaurate copolymer; acrylates/ acetoacetoxyethyl methacrylate copolymer; acrylates/beheneth-25 methacrylate copolymer; acrylates/C10-C30 alkyl acrylate crosspolymer; acrylates/ceteth-20 itaconate copolymer; acrylates/ceteth-20 methacrylate copolymer; acrylates/ laureth-25 methacrylate copolymer; acrylates/palmeth-25 acrylate copolymer; acrylates/palmeth-25 itaconate copolymer; acrylates/steareth-50 acrylate copolymer; acrylates/steareth-20 itaconate copolymer; acrylates/steareth-20 methacrylate copolymer; acrylates/stearyl methacrylate copolymer; acrylates/vinyl isodecanoate crosspolymer; acrylic acid/acrylonitrogens copolymer; adipic acid/methyl DEA crosspolymer; agar; agarose; *alcaligenes* polysaccharides; algin; alginic acid; almondamide DEA; almondamidopropyl betaine; aluminum/magnesium hydroxide stearate; ammonium acrylates/acrylonitrogens copolymer; ammonium acrylates copolymer; ammonium acryloyldimethyltaurate/vinyl formamide copolymer; ammonium acryloyldimethyltaurate/VP copolymer; ammonium alginate; ammonium chloride; ammonium polyacryloyldimethyl taurate; ammonium sulfate; amylopectin; apricotamide DEA; apricotamidopropyl betaine; arachidyl alcohol; arachidyl glycol; *arachis hypogaea* (peanut) flour; ascorbyl methylsilanol pectinate; *astragalus* gummifer gum; attapulgite; *avena sativa* (oat) kernel flour; avocadamide DEA; avocadamidopropyl betaine; azelamide MEA; babassuamide DEA; babassuamide MEA; babassuamidopropyl betaine; behenamide DEA; behenamide MEA; behenamidopropyl betaine; behenyl betaine; bentonite; butoxy chitosan; caesalpinia spinosa gum; calcium alginate; calcium carboxymethyl cellulose; calcium carrageenan; calcium chloride; calcium potassium carbomer; calcium starch octenylsuccinate; C20-40 alkyl stearate; canolamidopropyl betaine; capramide DEA; capryl/capramidopropyl betaine; carbomer; carboxybutyl chitosan; carboxymethyl cellulose acetate butyrate; carboxymethyl chitin; carboxymethyl chitosan; carboxymethyl dextran; carboxymethyl hydroxyethylcellulose; carboxymethyl hydroxypropyl guar; carnitine; cellulose acetate propionate carboxylate; cellulose gum; ceratonia siliqua gum; cetearyl alcohol; cetyl alcohol; cetyl babassuate; cetyl betaine; cetyl glycol; cetyl hydroxyethylcellulose; chimyl alcohol; cholesterol/HDI/pullulan copolymer; cholesteryl hexyl dicarbamate pullulan; citrus aurantium dulcis (orange) peel extract; cocamide DEA; cocamide MEA; cocamide MIPA; cocamidoethyl betaine; cocamidopropyl betaine; cocamidopropyl hydroxysultaine; coco-betaine; coco-hydroxysultaine; coconut alcohol; coco/oleamidopropyl betaine; cocoSultaine; cocoyl sarcosinamide DEA; cornamide/cocamide DEA; cornamide DEA; croscarmellose; crosslinked *bacillus*/ glucose/sodium glutamate ferment; *cyamopsis tetragonoloba* (guar) gum; decyl alcohol; decyl betaine; dehydroxanthan gum; dextrin; dibenzylidene sorbitol; diethanolaminooleamide DEA; diglycol/CHDM/isophthalates/SIP copolymer; dihydroabietyl behenate; dihydrogenated tallow benzylmonium hectorite; dihydroxyaluminum amino acetate; dimethicone/PEG-10 crosspolymer; dimethicone/PEG-15 crosspolymer; dimethicone propyl PG-betaine; dimethylacrylamide/acrylic acid/polystyrene ethyl methacrylate copolymer; dimethylacrylamide/sodium acryloyldimethyltaurate crosspolymer; disteareth-100 IPDI; DMAPA acrylates/acrylic acid/acrylonitrogens copolymer; erucamidopropyl hydroxysultaine; ethylene/sodium acrylate copolymer; gelatin; gellan gum; glyceryl alginate; glycine soja (soybean) flour; guar hydroxypropyltrimonium chloride; hectorite; hyaluronic acid; hydrated silica; hydrogenated potato starch; hydrogenated tallow; hydrogenated tallowamide DEA; hydrogenated tallow betaine; hydroxybutyl methylcellulose; hydroxyethyl acrylate/sodium acryloyldimethyl taurate copolymer; hydroxyethylcellulose; hydroxyethyl chitosan; hydroxyethyl ethylcellulose; hydroxyethyl stearamide-MIPA; hydroxylauryl/hydroxymyristyl betaine; hydroxypropylcellulose; hydroxypropyl chitosan; hydroxypropyl ethylenediamine carbomer; hydroxypropyl guar;

hydroxypropyl methylcellulose; hydroxypropyl methylcellulose stearoxy ether; hydroxypropyl starch; hydroxypropyl starch phosphate; hydroxypropyl xanthan gum; hydroxystearamide MEA; isobutylene/sodium maleate copolymer; isostearamide DEA; isostearamide MEA; isostearamide mIPA; isostearamidopropyl betaine; lactamide MEA; lanolinamide DEA; lauramide DEA; lauramide MEA; lauramide MIPA; lauramide/myristamide DEA; lauramidopropyl betaine; lauramidopropyl hydroxysultaine; laurimino bispropanediol; lauryl alcohol; lauryl betaine; lauryl hydroxysultaine; lauryl/myristyl glycol hydroxypropyl ether; lauryl sultaine; lecithinamide DEA; linoleamide DEA; linoleamide MEA; linoleamide MIPA; lithium magnesium silicate; lithium magnesium sodium silicate; *macrocystic pyrifera* (kelp); magnesium alginate; magnesium/aluminum/hydroxide/carbonate; magnesium aluminum silicate; magnesium silicate; magnesium trisilicate; methoxy PEG-22/dodecyl glycol copolymer; methylcellulose; methyl ethylcellulose; methyl hydroxyethylcellulose; microcrystalline cellulose; milkamidopropyl betaine; minkamide DEA; minkamidopropyl betaine; MIPA-myristate; montmorillonite; Moroccan lava clay; myristamide DEA; myristamide MEA; myristamide MIPA; myristamidopropyl betaine; myristamidopropyl hydroxysultaine; myristyl alcohol; myristyl betaine; natto gum; nonoxynyl hydroxyethylcellulose; oatamide MEA; oatamidopropyl betaine; octacosanyl glycol isostearate; octadecene/MA copolymer; oleamide DEA; oleamide MEA; oleamide MIPA; oleamidopropyl betaine; oleamidopropyl hydroxysultaine; oleyl betaine; olivamide DEA; olivamidopropyl betaine; oliveamide MEA; palmamide DEA; palmamide MEA; palmamide MIPA; palmamidopropyl betaine; palmitamide DEA; palmitamide MEA; palmitamidopropyl betaine; palm kernel alcohol; palm kernelamide DEA; palm kernelamide MEA; palm kernelamide MIPA; palm kernelamidopropyl betaine; peanutamide MEA; peanutamide MIPA; pectin; PEG-800; PEG-crosspolymer; PEG-150/decyl alcohol/SMDI copolymer; PEG-175 diisostearate; PEG-190 distearate; PEG-15 glyceryl tristearate; PEG-140 glyceryl tristearate; PEG-240/HDI copolymer bis-decyltetradeceth-20 ether; PEG-100/IPDI copolymer; PEG-180/laureth-50/TMMG copolymer; PEG-10/lauryl dimethicone crosspolymer; PEG-15/lauryl dimethicone crosspolymer; PEG-2M; PEG-5M; PEG-7M; PEG-9M; PEG-14M; PEG-20M; PEG-23M; PEG-25M; PEG-45M; PEG-65M; PEG-90M; PEG-115M; PEG-160M; PEG-180M; PEG-120 methyl glucose trioleate; PEG-180/octoxynol-40/TMMG copolymer; PEG-150 pentaerythrityl tetrastearate; PEG-4 rapeseedamide; PEG-150/stearyl alcohol/SMDI copolymer; *phaseolus angularis* seed powder; *polianthes tuberosa* extract; polyacrylate-3; polyacrylic acid; polycyclopentadiene; polyether-1; polyethylene/isopropyl maleate/MA copolyol; polyglyceryl-3 disiloxane dimethicone; polyglyceryl-3 polydimethylsiloxyethyl dimethicone; polymethacrylic acid; polyquaternium-52; polyvinyl alcohol; potassium alginate; potassium aluminum polyacrylate; potassium carbomer; potassium carrageenan; potassium chloride; potassium palmate; potassium polyacrylate; potassium sulfate; potato starch modified; PPG-2 cocamide; PPG-1 hydroxyethyl caprylamide; PPG-2 hydroxyethyl cocamide; PPG-2 hydroxyethyl coco/isostearamide; PPG-3 hydroxyethyl soyamide; PPG-14 laureth-60 hexyl dicarbamate; PPG-14 laureth-60 isophoryl dicarbamate; PPG-14 palmeth-60 hexyl dicarbamate; propylene glycol alginate; PVP/decene copolymer; PVP montmorillonite; *pyrus cyclonia* seed; *pyrus malus* (apple) fiber; rhizobian gum; ricebranamide DEA; ricinoleamide DEA; ricinoleamide MEA; ricinoleamide MIPA; ricinoleamidopropyl betaine; ricinoleic acid/adipic acid/AEEA copolymer; *rosa multiflora* flower wax; sclerotium gum; sesamide DEA; sesamidopropyl betaine; sodium acrylate/acryloyldimethyl taurate copolymer; sodium acrylates/acrolein copolymer; sodium acrylates/acrylonitrogens copolymer; sodium acrylates copolymer; sodium acrylates crosspolymer; sodium acrylate/sodium acrylamidomethylpropane sulfonate copolymer; sodium acrylates/vinyl isodecanoate crosspolymer; sodium acrylate/vinyl alcohol copolymer; sodium carbomer; sodium carboxymethyl chitin; sodium carboxymethyl dextran; sodium carboxymethyl beta-glucan; sodium carboxymethyl starch; sodium carrageenan; sodium cellulose sulfate; sodium chloride; sodium cyclodextrin sulfate; sodium hydroxypropyl starch phosphate; sodium isooctylene/MA copolymer; sodium magnesium fluorosilicate; sodium oleate; sodium palmitate; sodium palm kernelate; sodium polyacrylate; sodium polyacrylate starch; sodium polyacryloyldimethyl taurate; sodium polygamma-glutamate; sodium polymethacrylate; sodium polystyrene sulfonate; sodium silicoaluminate; sodium starch octenylsuccinate; sodium stearate; sodium stearoxy PG-hydroxyethylcellulose sulfonate; sodium styrene/acrylates copolymer; sodium sulfate; sodium tallowate; sodium tauride acrylates/acrylic acid/acrylonitrogens copolymer; sodium tocopheryl phosphate; *solanum tuberosum* (potato) starch; soyamide DEA; soyamidopropyl betaine; starch/acrylates/acrylamide copolymer; starch hydroxypropyltrimonium chloride; stearamide AMP; stearamide DEA; stearamide DEA-distearate; stearamide DIBA-stearate; stearamide MEA; stearamide MEA-stearate; stearamide MIPA; stearamidopropyl betaine; steareth-60 cetyl ether; steareth-100/PEG-136/HDI copolymer; stearyl alcohol; stearyl betaine; sterculia urens gum; synthetic fluorphlogopite; tallamide DEA; tallow alcohol; tallowamide DEA; tallowamide MEA; tallowamidopropyl betaine; tallowamidopropyl hydroxysultaine; tallowamine oxide; tallow betaine; tallow dihydroxyethyl betaine; tamarindus indica seed gum; tapioca starch; TEA-alginate; TEA-carbomer; TEA-hydrochloride; trideceth-2 carboxamide MEA; tridecyl alcohol; triethylene glycol dibenzoate; trimethyl pentanol hydroxyethyl ether; *triticum vulgare* (wheat) germ powder; *triticum vulgare* (wheat) kernel flour; *triticum vulgare* (wheat) starch; tromethamine acrylates/acrylonitrogens copolymer; tromethamine magnesium aluminum silicate; undecyl alcohol; undecylenamide DEA; undecylenamide MEA; undecylenamidopropyl betaine; welan gum; wheat germamide DEA; wheat germamidopropyl betaine; xanthan gum; yeast beta-glucan; yeast polysaccharides and *zea mays* (corn) starch.

One preferred co-thickener are polymers having the INCI names acrylates/C10-30 alkyl acrylate crosspolymer and acrylates copolymer. These polymers are known in the art under the brand name Carbopol® and are commercially available by The Lubrizol Corporation. Specific variants of Carbopol® include Carbopol® Aqua SF-1, Carbopol® Aqua SF-2, Carbopol® Aqua CC, Carbopol® Ultrez 10, and Carbopol® Ultrez 20.

Additional examples of thickeners are provided in WO 2009/107073, which is hereby incorporated in its entirety by reference.

Product Forms

Many different product forms lend themselves to the hair color products of the present invention. For example, color base may take the form of a liquid or gel and be stored in glass or plastic bottles, or metal or plastic tubes, while a developer also may take the form of a liquid or gel and also be provided in plastic bottles. Immediately prior to application, the color base is combined with the developer by pouring, blending, mixing, shaking, or squeezing the contents into the plastic container that contains the developer mixture. Then, the two compositions are mixed well to give a thickened color mix. The plastic bottle provides a convenient method for delivering the color mix to the keratin fibers (particularly to the base of any untreated fibers).

One method related to this first product form is taught in U.S. Pat. No. 6,976,495, which is incorporated herein its entirety by reference. The method of the '495 patent is an applicator bottle suitable for coloring strands of the keratin fibers, for example for creating highlights, lowlights, or multi-hued tones.

Alternatively, the color base may take the form of a solid or powder packaged separately from a liquid or gel developer, which again is most conveniently provided in a plastic bottle. Solid or powdered color bases may contain the powdered form of the lightly- to moderately-crosslinked PVP, given by such disclosure as U.S. Pat. No. 5,139,770, which is incorporated herein its entirety by reference. Upon adding the color base into the developer bottle, the contents are thoroughly mixed to give the thickened color mix for application.

In yet another method, a single container holds the color base and the developer, being separated by a breakable or rupturable barrier. The at least two parts are mixed by the user after breaking the barrier so that the parts can be mixed together.

At least a fourth method is envisioned for supplying the hair color product—a single container wherein the color base and developer are individually and separately held, and are mixed together after exiting the container's delivery tip.

Method for Enhancing Performance

Included in the invention is a method for enhancing the on-hair performance of hair color products. Illustrative of this method, thickened color mixes according to the invention are applied to hair, and compared to control color mixes that do not contain lightly- to moderately-crosslinked PVP. The following attributes related to the application of the color mix are rated: spreadability, ease of application, smooth feel, clean feel, and tendency for dripping/running Similarly, attributed related to hair color features also are rated: color uniformity, color density, hair shine, hair softness, hair manageability and overall appearance.

Unexpectedly, addition of lightly- to moderately-crosslinked PVP improved these attributes to a perceptible extent over the control. Due in part to the enhanced rheology of the color mix, the method improves the ease, uniformity, coverage, retention, and contact of the color mix with hair. For these reasons the method improves the ability for someone to color his/her own hair, particularly for curly or wavy hair, or hair on the back or sides of the head.

EXAMPLES

Example 1

Concentration Stability of Thickened Hydrogen Peroxide Solutions

Hydrogen peroxide (35% solution, Degussa) was blended with increasing levels of freshly prepared solutions of lightly- to moderately-crosslinked PVP in deionized water. After blending, the initial concentration of hydrogen peroxide in all samples was 6% (w/w). Then, aliquots were transferred to clean, translucent polyethylene terephthalate (PET) containers with tightly-fitting screw cap lids and stored for three months under the following six conditions: refrigerator at 5° C., laboratory shelf at 25° C., laboratory oven at 40° C., laboratory oven at 50° C., laboratory window exposed to natural sunlight, and −20° C./25° C. freeze/thaw cycles. Hydrogen peroxide concentrations after 1, 2, and 3 months were measured by titrating with 0.1 N potassium after heating the blends for 24 hours at 100° C. The control sample was a 6% (w/w) hydrogen peroxide solution made in deionized water without added polymer.

Lightly- to moderately-crosslinked PVP did not promote instability of the hydrogen peroxide concentration, since the concentration of the test conditions did not differ from the control (FIGS. 1-6).

Example 2

Stability of Viscosity of Thickened Hydrogen Peroxide Solutions

Hydrogen peroxide solutions of Example 1 also were tested for viscosity stability. The viscosities of stored samples were measured at 25° C. using a Brookfield DV2 viscometer with spindle RV3 operating at 10 revolutions per minute (rpm).

Hydrogen peroxide solutions thickened with lightly- to moderately-crosslinked PVP exhibit stable viscosity profiles for the test conditions of this example (FIGS. 7-12). A decline in viscosity of 500 cP and 1000 cP after 1 month was measured for the conditions stored at 50° C. and the freeze/thaw cycle, respectively. However, even these samples showed stable viscosity after 1 month.

Hydrogen peroxide solutions containing 4% of the lightly- to moderately-crosslinked PVP displayed exceptional thickness, with viscosities of 3500 cP, 4000 cP, or even 4500 cP or more.

Example 3

Stability of pH of Thickened Hydrogen Peroxide Solutions

Hydrogen peroxide solutions of Example 1 also were tested for pH stability. The pH of stored samples were measured using a Thermo Orion pH meter, model 420A+.

Hydrogen peroxide solutions thickened with lightly- to moderately-crosslinked PVP exhibit stable pH profiles for the test conditions of this example (FIGS. 13-17). These pH-stable solutions were acidic, having a pH between 4.95 and 5.13.

Comparative Example 1

Three commercial hair colors (denoted #1, #2, and #3) were selected to study the viscosities and pH of the color base, the developer, and the color mix after blending the color base with the developer. The selected commercial products represent different hair color technologies in terms of the alkaline color base and thickeners. Table 1 summarizes the color base and developer ingredients, as provided on the box label. In this comparative example lightly- to moderately-crosslinked PVP was not added to the commercial hair colors. Viscosity was measured at room temperature (25° C.) using a Brookfield DV2 viscometer with a RV3 spindle (unless noted otherwise), operating at 10 rpm. For each composition the pH was measured neat (meaning without dilution) using a Thermo Orion pH meter, model 420A+.

Table 2 presents the pH and viscosities for these commercial hair colors.

TABLE 1

Listed ingredients in the three studied commercial hair colors.

| commercial hair color | commercial color base form | type | thickening technology |
|---|---|---|---|
| #1 | liquid | ammonia-based | Sufficient viscosity of color mix attained after blending color base with developer (in part, via neutralization of acrylic polymer). |
| #2 | cream | ammonia-based | Color base and developer already are thickened. |
| #3 | liquid | ammonia-free | Sufficient viscosity of color mix attained after blending color base with developer (in part, via neutralization of acrylic polymer). |

TABLE 2

Measured pH and viscosity for three commercial hair colors.

| | commercial color base | | commercial developer | | commercial color mix | |
|---|---|---|---|---|---|---|
| commercial hair color | pH | viscosity (cP) | pH | viscosity (cP) | pH | viscosity (cP) |
| #1 | 10.35 | 0 | 3.14 | 0 | 9.67 | 7,930 |
| #2 | 10.31 | 24,080 | 2.47 | 2,100 | 9.76 | 4,200 |
| #3 | 10.52 | 100 | 3.79 | 2,430 | 9.96 | 4,900 |

Example 4

Effect of Adding 3% Lightly- to Moderately-Crosslinked PVP to the Color Bases of Commercial Hair Colors #1, #2, and #3

The three commercial hair colors of Comparative Example 1 were reformulated by adding 3% (w/w color base) lightly- to moderately-crosslinked PVP to the color base. Incorporating the lightly- to moderately-crosslinked PVP into the color base was facilitated by use of a high-speed homogenizer. Once the color base was thickened, the customary method was used for blending the color base and the developer. The pH and viscosities were measured as described in Comparative Example 1.

Adding the lightly- to moderately-crosslinked PVP increased the viscosity of the color bases (Table 3). The changes in viscosity for all three color bases were unexpected, since water containing 3% lightly crosslinked PVP has a viscosity of +2,300 cP. Commercial hair colors #1 and #3 exhibited less-than-expected increases, while the color base viscosity of the thickened color base #2 increased +81,800 cP. Without being bound by theory, an associative thickening synergy is believed to exist between the lightly crosslinked PVP and the ingredients of the color base #2 noted in Comparative Example 1.

Even more unexpected were the resulting viscosities for the reformulated color mix. All three reformulated color mixes had significantly higher viscosity than the commercial product values (Table 3). Commercial hair colors #1 and #3 attained color mix viscosities greater than 20,000 cP. The increases in color mix viscosities (Tables 1 and 2) were not a linear addition of the commercial developer to the color base +3% lightly crosslinked PVP. Instead, it is believed that another associative thickening synergy exists between the color base ingredient(s), the lightly crosslinked PVP, and the commercial developers, particularly for hair colors #1 and #3.

TABLE 3

Measured pH and viscosity for three commercial hair colors with 3% lightly- to moderately-crosslinked PVP added to the color base.

| | color base + 3% lightly- to moderately-crosslinked PVP | | commercial developer | | color mix | |
|---|---|---|---|---|---|---|
| commercial hair color | pH | viscosity (cP) | pH | viscosity (cP) | pH | viscosity (cP) |
| #1 | 9.55 | 1,160 | 3.14 | 0 | 8.61 | 53,000* |
| #2 | 10.35 | 81,800 | 2.47 | 2,100 | 9.81 | 8,700* |
| #3 | 10.44 | 400 | 3.79 | 2,430 | 9.98 | 27,700* |

*RV6 spindle

Example 5

Effect of Adding 5% Lightly- to Moderately-Crosslinked PVP to the Color Base of Commercial Hair Colors #1, #2, and #3

As in Example 1, the three commercial hair colors of Comparative Example 1 were reformulated, but time with 5% (w/w color base) lightly- to moderately-crosslinked PVP added to the color base. The pH and viscosities were measured as described in Comparative Example 1.

Further increases in color base and color mix viscosities were measured (Table 4).

TABLE 4

Measured pH and viscosity for three commercial hair colors with 5% lightly- to moderately-crosslinked PVP added to the developer.

| | color base + 5% lightly- to moderately-crosslinked PVP | | commercial developer | | color mix | |
|---|---|---|---|---|---|---|
| commercial hair color | pH | viscosity (cP) | pH | viscosity (cP) | pH | viscosity (cP) |
| #1 | 9.5 | 3,370 | 3.14 | 0 | 8.76 | 65,600* |
| #2 | 10.29 | 87,000 | 2.47 | 2,100 | 9.76 | 15,900* |
| #3 | 10.46 | 1,370 | 3.79 | 2,430 | 9.96 | 37,000* |

*RV6 spindle

Comparative Example 2

Commercial Hair Colors with a Generic Developer

The three commercial hair colors of Comparative Example 1 were studied again, but this time the commercial developer was replaced by a generic developer, being 6% hydrogen peroxide aqueous solution. The viscosities and pH of each part and the blend of the commercial color base with the generic developer were measured as described in Comparative Example 1.

Table 5 presents the values for these commercial hair colors.

TABLE 5

Measured pH and viscosity for three commercial hair colors.

| commercial hair color | commercial color base | | generic developer | | color mix | |
|---|---|---|---|---|---|---|
| | pH | viscosity (cP) | pH | viscosity (cP) | pH | viscosity (cP) |
| #1 | 10.35 | 0 | 3.49 | 0 | 9.86 | 0 |
| #2 | 10.31 | 24,080 | 3.49 | 0 | 9.76 | 2,350 |
| #3 | 10.52 | 100 | 3.49 | 0 | 10.02 | 900 |

Example 6

Effect of Adding 3% Lightly- to Moderately-Crosslinked PVP to the Color Base of Commercial Hair Colors #1, #2, and #3 Using a Generic Developer As in Example 4 the three commercial hair colors were reformulated by adding 3% (w/w color base) lightly- to moderately-crosslinked PVP to color base. In this example, however, the commercial developer was replaced by a generic, 6% hydrogen peroxide aqueous solution (unthickened). The pH and viscosities were measured as described in Comparative Example 1.

Upon blending the color base (containing 3% lightly crosslinked PVP) and the generic developer, a thickened color mix was attained (Table 6). The color mixes were substantially more viscous than those of Comparative Example 2 (Table 5).

TABLE 6

Measured pH and viscosity for three commercial hair colors with 3% lightly- to moderately-crosslinked PVP added to the color base and using a generic developer.

| commercial hair color | color base + 3% lightly cross-linked PVP | | generic developer (6% $H_2O_2$ solution) | | color mix | |
|---|---|---|---|---|---|---|
| | pH | viscosity (cP) | pH | viscosity (cP) | pH | viscosity (cP) |
| #1 | 9.55 | 1,160 | 3.49 | 0 | 9.8 | 550 |
| #2 | 10.35 | 81,800 | 3.49 | 0 | 9.7 | 7,400 |
| #3 | 10.44 | 400 | 3.49 | 0 | 10.0 | 3,100 |

Example 7

Effect of Adding 5% Lightly- to Moderately-Crosslinked PVP to the Color Base of Commercial Hair Colors #1, #2, and #3 Using a Generic Developer As in Example 5 the three commercial hair colors were reformulated by adding 5% (w/w color base) lightly- to moderately-crosslinked PVP to color base. In this example, however, the commercial developer was replaced by a generic 6% hydrogen peroxide aqueous solution (unthickened). The pH and viscosities were measured as described in Comparative Example 1.

Color mixes were produced having higher viscosities than Comparative Example 2 and Example 3 (Table 7).

TABLE 7

Measured pH and viscosity for three commercial hair colors with 5% lightly- to moderately-crosslinked PVP added to the color base and using a generic developer.

| commercial hair color | color base + 5% lightly cross-linked PVP | | generic developer (6% $H_2O_2$ solution) | | color mix | |
|---|---|---|---|---|---|---|
| | pH | viscosity (cP) | pH | viscosity (cP) | pH | viscosity (cP) |
| #1 | 9.5 | 3,370 | 3.49 | 0 | 9.85 | 1,400 |
| #2 | 10.29 | 87,000 | 3.49 | 0 | 9.69 | 11,700 |
| #3 | 10.46 | 1,370 | 3.49 | 0 | 9.97 | 6,900 |

Example 8

Effect of Adding Lightly- to Moderately-Crosslinked PVP to 6% Hydrogen Peroxide Solution Because commercial hair color formulations frequently contain a hydrogen peroxide-based developer, it was important to understand the relationship of lightly- to moderately-crosslinked PVP addition on hydrogen peroxide viscosity. For this study, the lightly- to moderately-crosslinked PVP was added to 6% hydrogen peroxide solution created by diluting 35% hydrogen peroxide solution with deionized water. Measurements were made using a Brookfield DV2 viscometer at 25° C. and 10 rpm with spindle RV3.

Figure 18:
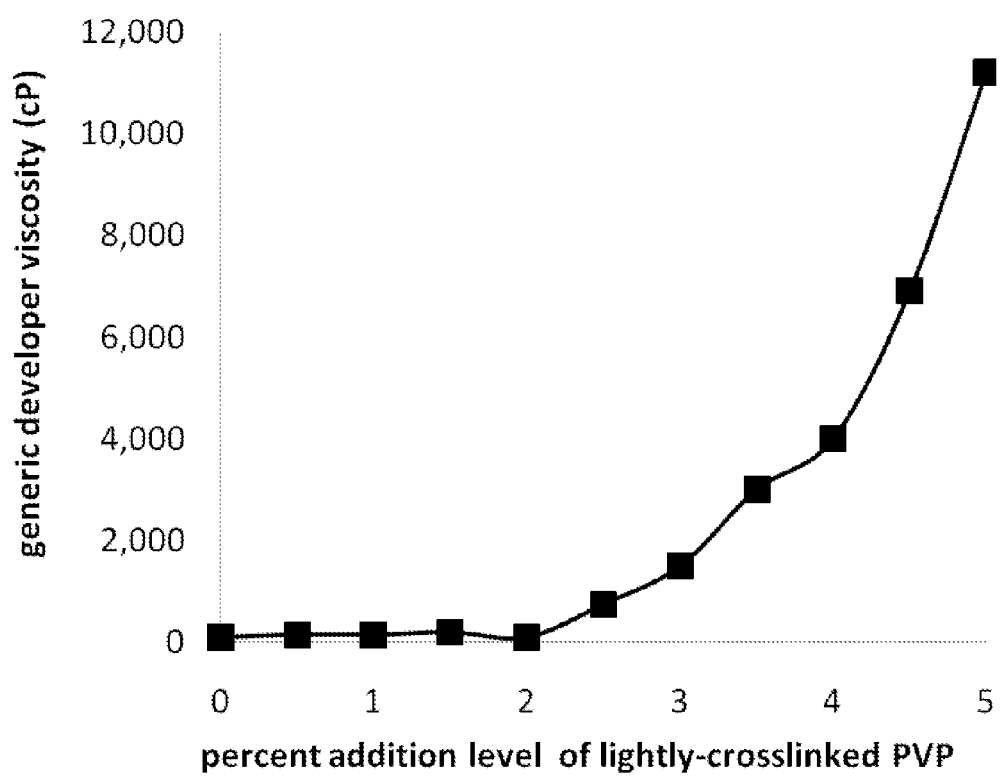
FIG. 18 is a graph of generic developer viscosity as a function of lightly- to moderately-crosslinked PVP addition produced in accordance with Example 8.
Figure 19:
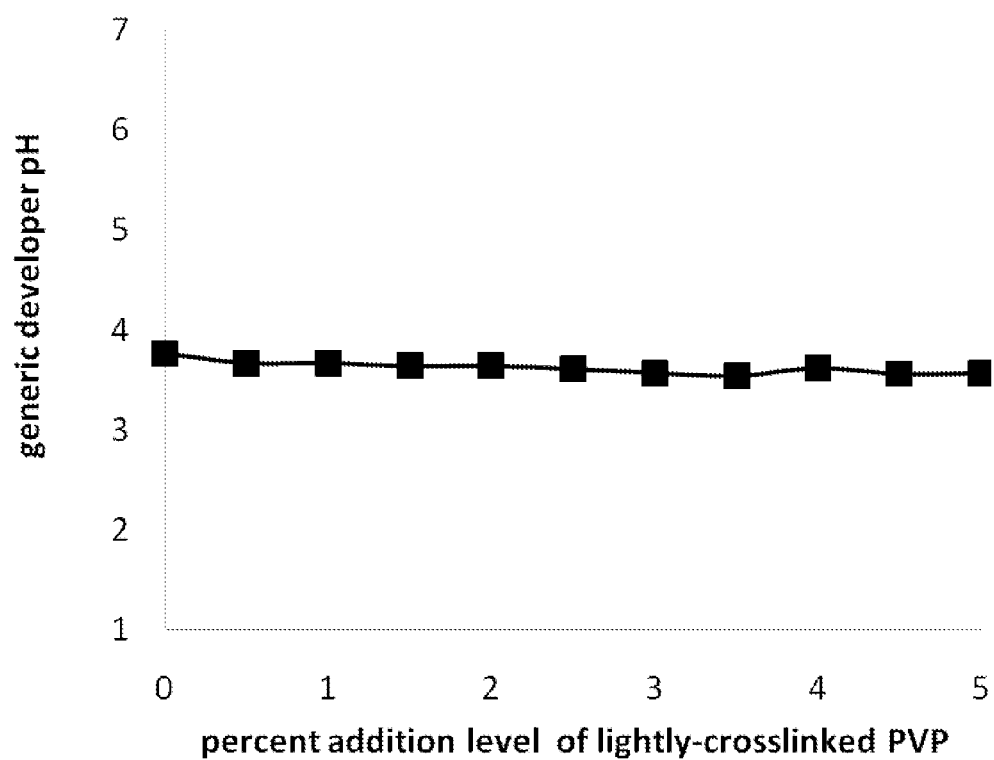
FIG. 19 is a graph of generic developer pH as a function of lightly- to moderately-crosslinked PVP addition produced in accordance with Example 8.

The results show that the generic hydrogen peroxide developer had a viscosity of about 100 cP to 200 cP with 2% (w/w generic developer solution) addition of lightly- to moderately-crosslinked PVP (FIG. 18). A substantial build in viscosity occurred with higher addition levels. At 3% (w/w) polymer addition the viscosity was 1,500 cP, and at 5% (w/w developer solution) polymer addition the viscosity was 11,200 cP. Additionally, the pH of the thickened hydrogen peroxide solution remained stable (FIG. 19).

Example 9

Effect of Adding Lightly- to Moderately-Crosslinked PVP to the Color Base of Commercial Hair Colors #1, #2, and #3

Lightly- to moderately-crosslinked PVP was added from 2.5% (w/w color base) to 6% (w/w color base) to the commercial color bases of Comparative Example 1, and the viscosity measured using a Brookfield DV2 viscometer with RV6 spindle operating at 10 rpm.

Figure 20:
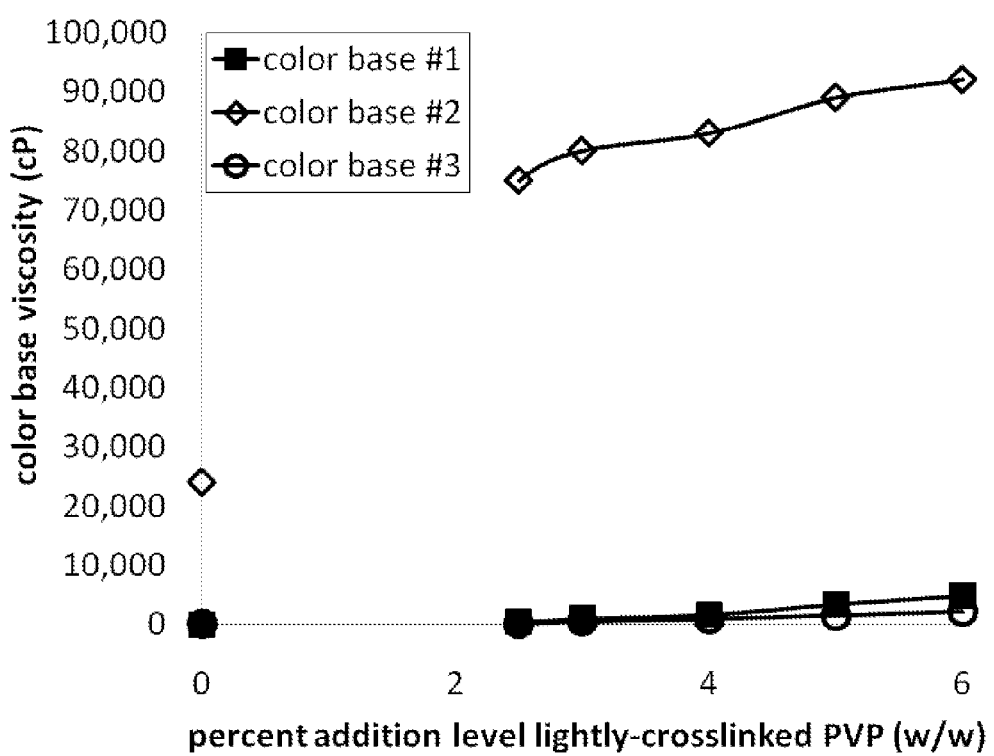
FIG. 20 is a graph of color base viscosity as a function of lightly- to moderately-crosslinked PVP addition produced in accordance with Example 9.

The measurements show that lightly- to moderately-crosslinked PVP increased the viscosity of the three color bases (FIG. 20). As noted in Example 4, the effect is particularly pronounced with hair color #2. This color base contained a fatty alcohol and took the form of an emulsion cream. The associative thickening between lightly- to moderately-crosslinked PVP and such color bases was unexpected.

Example 10

Effect of Adding Lightly- to Moderately-Crosslinked PVP to a Hair Color Created from a Generic Developer Lightly- to moderately-crosslinked PVP was added from 2.5% (w/w developer) to 4.5% (w/w developer) to a generic developer that was 6% hydrogen peroxide aqueous solution. Then, this developer was blended with the three commercial color bases of Comparative Example 1, and the pH and viscosities were measured using the method of Comparative Example 1.

Figure 21:
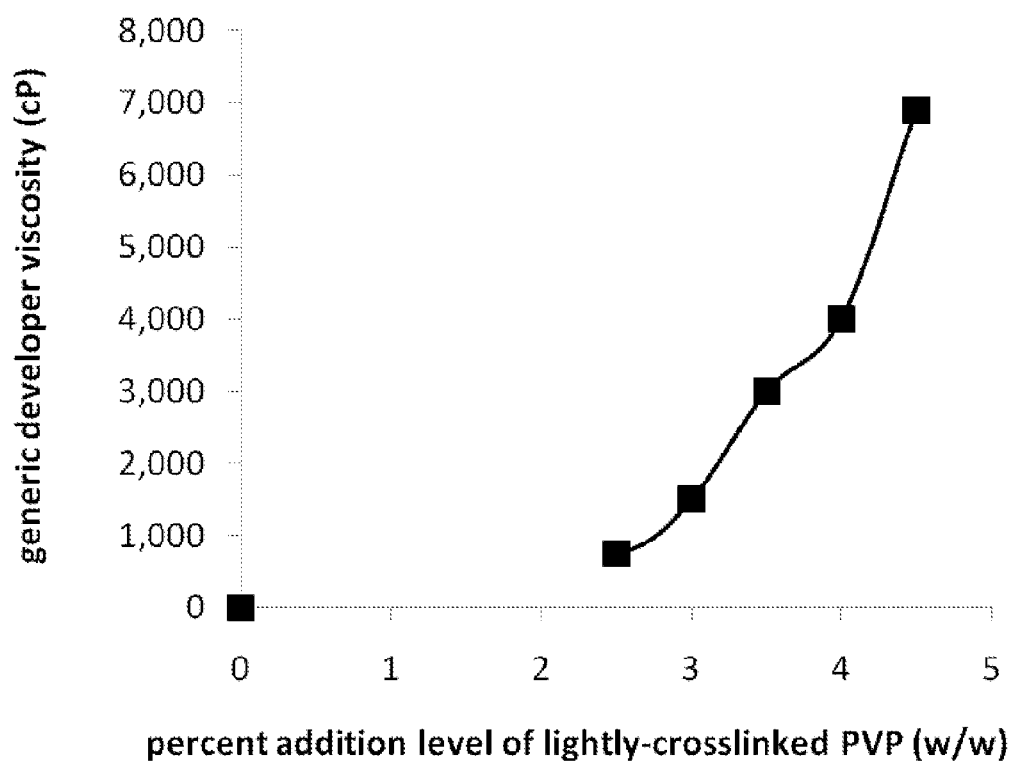
FIG. 21 is a graph of generic developer viscosity as a function of lightly- to moderately-crosslinked PVP addition produced in accordance with Example 10.

Results for the commercial hair colors #1, #2, and #3 (Tables 8-10) show the following discoveries:

First, lightly- to moderately-crosslinked PVP effectively thickened the 6% hydrogen peroxide solution, attaining a Brookfield viscosity of almost 7,000 cP when measured at 10 rpm with the RV3 spindle (FIG. 21). At the same time, the thickened generic developer solution maintained a pH of about 3.6 over this range in viscosity.

Figure 22:
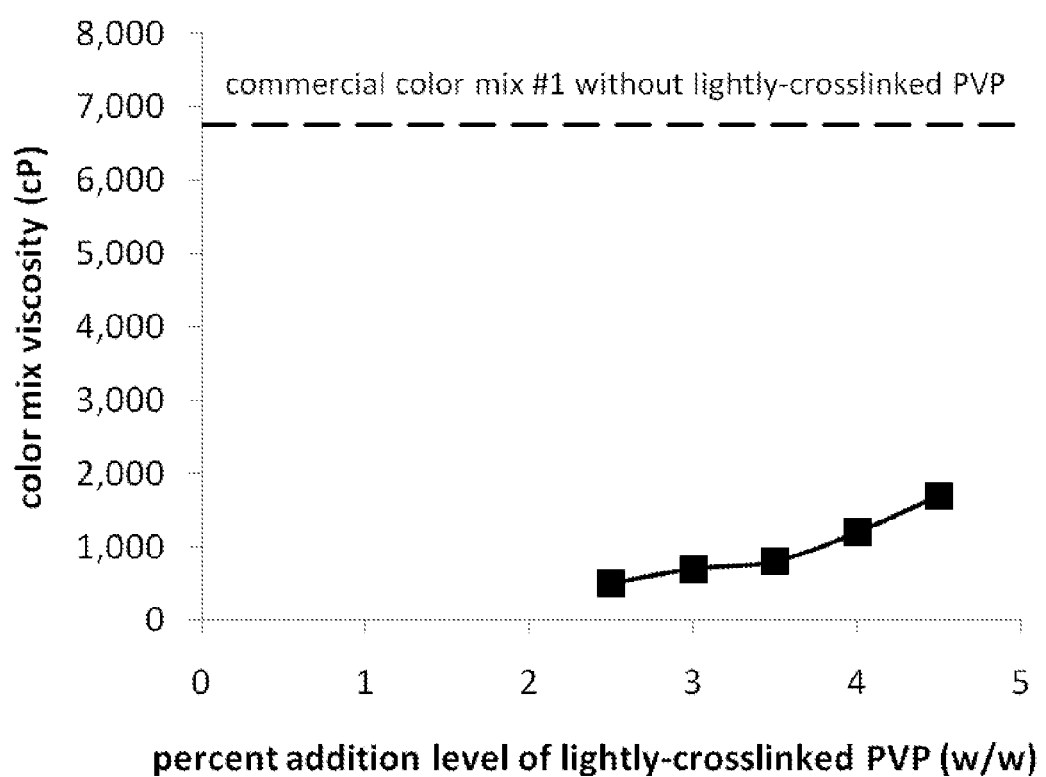
FIG. 22 is a graph of color mix viscosity as a function of lightly- to moderately-crosslinked PVP addition produced in accordance with Example 10.
Figure 23:
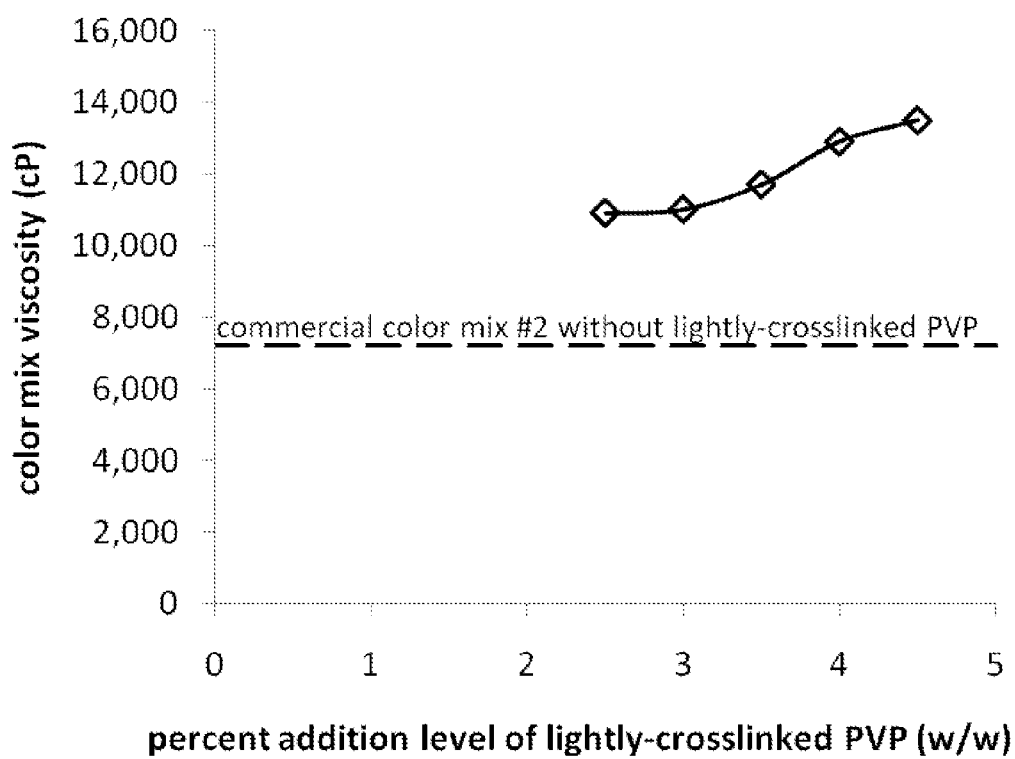
FIG. 23 is a graph of color mix viscosity as a function of lightly- to moderately-crosslinked PVP addition produced in accordance with Example 10.
Figure 24:
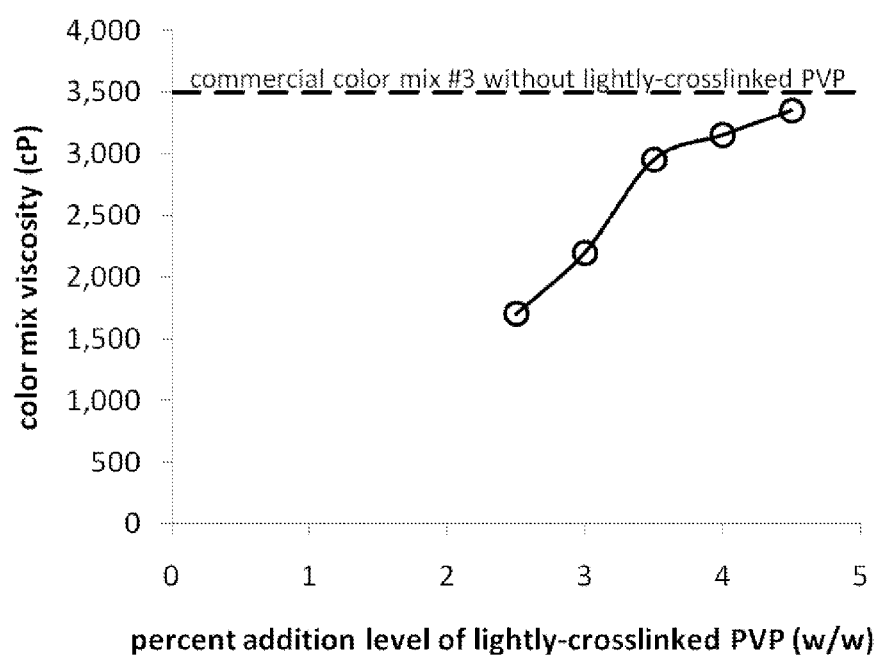
FIG. 24 is a graph of color mix viscosity as a function of lightly- to moderately-crosslinked PVP addition produced in accordance with Example 10.

Second, the final color mix viscosity depended was formulation specific. For example, color mix viscosities ranged from 500 cP to 1,700 cP for commercial hair color #1 (FIG. 22), from 10,900 cP to 13,500 cP for commercial hair color #2 (FIG. 23), and from 1,700 cP to 3,350 cP for commercial hair color #3 (FIG. 24). As taught in U.S. Pat. No. 7,481,846, the contents of which are incorporated herein their entirety by reference, color mixes having a viscosity of about 1,000 cP or more are generally regarded as acceptable for use, since color mix dripping is minimized at these viscosities.

One color mix of the invention reached viscosities higher than the commercial color mix. Color mix #2 was thickened to viscosities higher than the 7,200 cP that characterized the blended product of the commercial color base and the commercial developer. A similar effect was noted in the earlier Examples wherein lightly- to moderately-crosslinked PVP was added to the color base for commercial hair color #2. Again, this result suggests a favorable interaction between lightly- to moderately-crosslinked PVP and the commercial product's thickener system.

Third, the pH of the color mix remained essentially constant with increasing levels of lightly- to moderately-crosslinked PVP for the three commercial hair colors, suggesting formulation stability (Tables 8-10).

TABLE 8

Viscosity and pH measurements for lightly- to moderately-crosslinked PVP added to the developer of Commercial Hair Color #1

| color base: Commercial Hair Color #1 | | | | | | |
|---|---|---|---|---|---|---|
| pH: | 10.35 | 10.35 | 10.35 | 10.35 | 10.35 | 10.35 |
| viscosity (cP): | 0 | 0 | 0 | 0 | 0 | 0 |
| commercial developer: Commercial Hair Color #1 | | | | | | |
| pH: | 3.14 | | | | | |
| viscosity (cP): | 0 | | | | | |
| generic developer: 6% H$_2$O$_2$ Solution | | | | | | |
| lightly- to moderately-crosslinked PVP: | | 2.5% | 3.0% | 3.5% | 4.0% | 4.5% |
| pH: | | 3.61 | 3.57 | 3.54 | 3.62 | 3.56 |
| viscosity (cP): | | 750 | 1,500 | 3,000 | 4,000 | 6,900 |
| color base + developer | | | | | | |
| pH: | 9.67 | 9.98 | 9.75 | 9.76 | 9.97 | 9.82 |
| viscosity (cP): | 6,750 | 500 | 700 | 800 | 1,200 | 1,700 |

TABLE 9

Viscosity and pH measurements for lightly- to moderately-crosslinked PVP added to the developer of Commercial Hair Color #2

| color base: Commercial Hair Color #1 | | | | | | |
|---|---|---|---|---|---|---|
| pH: | 10.3 | 10.3 | 10.3 | 10.3 | 10.3 | 10.3 |
| viscosity (cP): | 24,000 | 24,000 | 24,000 | 24,000 | 24,000 | 24,000 |
| commercial developer: Commercial Hair Color #1 | | | | | | |
| pH: | 2.47 | | | | | |
| viscosity (cP): | 2,110 | | | | | |
| generic developer: 6% H$_2$O$_2$ Solution | | | | | | |
| lightly- to moderately-crosslinked PVP: | | 2.5% | 3.0% | 3.5% | 4.0% | 4.5% |
| pH: | | 3.61 | 3.57 | 3.54 | 3.62 | 3.56 |
| viscosity (cP): | | 750 | 1,500 | 3,000 | 4,000 | 6,900 |
| color base + developer | | | | | | |
| pH: | 9.72 | 9.77 | 9.76 | 9.69 | 9.8 | 9.76 |
| viscosity (cP): | 7,200 | 10,900 | 11,000 | 11,700 | 12,900 | 13,500 |

TABLE 10

Viscosity and pH measurements for lightly- to moderately-crosslinked PVP added to the developer of Commercial Hair Color #3

| color base: Commercial Hair Color #1 | | | | | | |
|---|---|---|---|---|---|---|
| pH: | 10.5 | 10.5 | 10.5 | 10.5 | 10.5 | 10.5 |
| viscosity (cP): | 150 | 150 | 150 | 150 | 150 | 150 |
| commercial developer: Commercial Hair Color #1 | | | | | | |
| pH: | 3.79 | | | | | |
| viscosity (cP): | 2,430 | | | | | |
| generic developer: 6% $H_2O_2$ Solution | | | | | | |
| lightly- to moderately-crosslinked PVP: | | 2.5% | 3.0% | 3.5% | 4.0% | 4.5% |
| pH: | | 3.61 | 3.57 | 3.54 | 3.62 | 3.56 |
| viscosity (cP): | | 750 | 1,500 | 3,000 | 4,000 | 6,900 |
| color base + developer | | | | | | |
| pH: | 9.72 | 9.77 | 9.76 | 9.69 | 9.8 | 9.76 |
| viscosity (cP): | 7,200 | 10,900 | 11,000 | 11,700 | 12,900 | 13,500 |

Example 11

Effect of Lightly- to Moderately-Crosslinked PVP on Hair Dying Performance

Salon studies are completed using commercial hair colors #1, #2, and #3 as described in Example 2. The hair colors (control and formulations as described herein) are applied on hair tresses by a licensed hair stylist. The ease of application (which includes drip- and run-avoidance) is rated by the cosmetologist. Similarly, the colored hair uniformity, color intensity, and hair shine also are rated.

The hair colors described herein are found not to drip nor run during application. Hair colored by the hair color compositions described herein exhibits stronger color intensity, more uniform color, and higher shine than hair treated with the control formulas. Further studies reveal that hair colored in accordance with the present application also resist color fading and loss of color intensity after multiple shampoo washes compared to a control hair color not having lightly- to moderately-crosslinked PVP.

What is claimed is:

1. A composition for coloring hair comprising either:
   A) a system comprising a color base and a developer wherein at least one of said color base and said developer comprises lightly- to moderately-crosslinked poly(N-vinyl-2-pyrrolidone (PVP); or
   B) a color mix wherein said color mix comprises lightly- to moderately-crosslinked poly(N-vinyl-2-pyrrolidone (PVP).

2. The composition according to claim 1 wherein said lightly- to moderately-crosslinked poly(N-vinyl-2-pyrrolidone (PVP) is present in an amount of up to 10% based on the total weight of said composition.

3. The composition according to claim 1 having a Brookfield viscosity from 50 cP to 100,000 cP measured at 25° C. at 10 rpm.

4. The composition according to claim 1 comprising an ingredient selected from the group consisting of: dyes, couplers, alkalizers, thickeners, alcohols, acids, surfactants, and combinations thereof.

5. The composition according to claim 1 wherein said color base or color mix comprises a dye selected from the group consisting of: m-aminophenol hydrochloride, p-aminophenol sulfate, 2,3-diaminophenol hydrochloride, 1,5-naphthalenediol, p-phenylenediamine hydrochloride, sodium picramate, a water-soluble cationic dye, a water soluble anionic dye, a water-soluble FD&C dye, Blue No. 1, Blue No. 2, Red No. 3, Red No. 4, Red No. 40, a water soluble D&C dye, Yellow No. 10, Red No. 22, Red No. 28, pyrogallol, 2-methyl-1,4-diaminobenzene, 2,6-dimethyl-1,4-diaminobenzene, 2,5-dimethyl-1,4-diaminobenzene, 2,3-dimethyl-1,4-diaminobenzene, 2-chloro-1,4-diaminobenzene, 2-methoxy-1,4-diaminobenzene, 1-phenylamino-4-aminobenzene, 1-dimethylamino-4-aminobenzene, 1-diethylamino-4-aminobenzene, 1-bis(beta-hydroxyethyl)amino-4-aminobenzene, 1-methoxyethylamino-4-aminobenzene, 2-hydroxymethyl-1,4-diaminobenzene, 2-hydroxyethyl-1,4-diaminobenzene, 2-isopropyl-1,4-diaminobenzene, 1-hydroxypropylamino-4-aminobenzene, 2,6-dimethyl-3-methoxy-1,4-diaminobenzene, 1-amino-4-hydroxybenzene, derivatives thereof; acid or basic salts thereof.

6. The composition according to claim 4 wherein said color base or color mix comprises a coupler selected from the group consisting of: resorcinol, 1-naphthol, phenyl methylpyrazolone, m-aminophenol, 4-amino-2-hydroxytoluene, 2-methylresorcinol, 1-naphthol, and combinations thereof.

7. The composition according to claim 4 wherein said color base or color mix comprises a thickener selected from the group consisting of: methyl cellulose, ethyl cellulose, hydroxyethyl cellulose, hydroxypropylmethyl cellulose, acrylates/C10-C30 alkyl acrylate crosspolymer, acrylates copolymer, and combinations thereof.

8. The composition according to claim 4 wherein said color base or color mix comprises an alkalizer selected from the group consisting of: ammonia, monoethanolamine, 2-amino-2-methylpropanol, sodium carbonate, and combinations thereof.

9. The composition according to claim 4 wherein said color base or color mix comprises an alcohol selected from the group consisting of: ethanol, 1-propanol, 2-propanol, oleyl alcohol, capryl alcohol, 2-ethylhexyl alcohol, pelargonic alcohol, capric alcohol, lauryl alcohol, myristyl alcohol, cetyl alcohol, stearyl alcohol, cetearyl alcohol, elaidyl alcohol, linoleyl alcohol, elaidolinolenyl alcohol, ricinoleyl alcohol, nonadecyl alcohol, arachidyl alcohol, behenyl alcohol, ceryl alcohol, montanyl alcohol, myricyl alcohol, geddyl alcohol, propylene glycol, glycerin, butylene glycol, hexylene glycol, sorbitol, and combinations thereof.

10. The composition according to claim 4 wherein said color base or color mix comprises an acid selected from the group consisting of: oleyl acid, capryl acid, 2-ethylhexyl acid, pelargonic acid, capric acid, lauric acid, myristic acid, cetylic (palmitic) acid, stearic acid, elaidic acid, linoleic acid, octadecadienoic acid, ricinoleic (ricinic) acid, nonadecylic acid, arachidonic acid, behenolic acid, cerotic (ceric) acid, montanic acid, myricic acid, geddic acid, and combinations thereof.

11. The composition according to claim 4 wherein said color base or color mix comprises a surfactant selected from the group consisting of: sodium lauryl sulfate, sodium laureth sulfate, and combinations thereof.

12. The composition according to claim 1 wherein said composition comprises the color base and developer.

13. The composition according to claim 12 wherein said lightly- to moderately-crosslinked poly(N-vinyl-2-pyrrolidone (PVP) is present in said developer in an amount of up to 10% based on the total weight of said developer. comprises lightly- to moderately-crosslinked PVP.

14. The composition according to claim 13 wherein said developer has a Brookfield viscosity from 50 cP to 25,000 cP measured at 25° C. at 10 rpm.

15. The composition according to claim 12 wherein said developer comprises an oxidizer selected from the group consisting of: hydrogen peroxide, sodium perborate, monoethanolamine, 2-amino-2-methylpropanol, sodium carbonate, urea peroxide, potassium persulfate, sodium persulfate, ammonium persulfate, and combinations thereof.

16. A method of coloring hair comprising:
   a. applying a color mix comprising lightly- to moderately-crosslinked poly(N-vinyl-2-pyrrolidone (PVP) to hair.

17. The method according to claim 16 wherein said color mix is formed by combining a color base and a developer.

18. The method according to claim 16 wherein said color mix is an oxidative color mix.

19. The method according to claim 16 wherein said lightly- to moderately-crosslinked poly(N-vinyl-2-pyrrolidone (PVP) is present in an amount of up to 10% based on the total weight of said color mix.

20. The method according to claim 19 wherein said color mix has a Brookfield viscosity from 50 cP to 100,000 cP measured at 25° C. at 10 rpm.

* * * * *